US011369488B2

(12) United States Patent
Su et al.

(10) Patent No.: US 11,369,488 B2
(45) Date of Patent: *Jun. 28, 2022

(54) UNICOMPARTMENTAL KNEE ARTHROPLASTY

(71) Applicant: ENGAGE UNI LLC, Orlando, FL (US)

(72) Inventors: Edwin P. Su, Scarsdale, NY (US);
Andrew D. Pearle, Rye, NY (US);
Daniel F. Justin, Orlando, FL (US);
Hyun Bae, Santa Monica, CA (US)

(73) Assignee: ENGAGE UNI LLC, Orlando, FL (US)

( * ) Notice: Subject to any disclaimer, the term of this patent is extended or adjusted under 35 U.S.C. 154(b) by 367 days.

This patent is subject to a terminal disclaimer.

(21) Appl. No.: 16/664,154

(22) Filed: Oct. 25, 2019

(65) Prior Publication Data

US 2020/0054462 A1    Feb. 20, 2020

Related U.S. Application Data

(63) Continuation of application No. 15/910,962, filed on Mar. 2, 2018, now Pat. No. 10,456,272.

(Continued)

(51) Int. Cl.
A61F 2/46    (2006.01)
A61F 2/38    (2006.01)
(Continued)

(52) U.S. Cl.
CPC .......... *A61F 2/461* (2013.01); *A61B 17/1615* (2013.01); *A61B 17/1659* (2013.01); *A61B 17/1764* (2013.01); *A61F 2/389* (2013.01); *A61B 17/1675* (2013.01); *A61B 2090/033* (2016.02); *A61F 2/30749* (2013.01); *A61F 2002/3071* (2013.01); *A61F 2002/30387* (2013.01); *A61F 2002/30878* (2013.01); *A61F 2002/30884* (2013.01); *A61F 2002/30894* (2013.01); *A61F 2002/3895* (2013.01); *A61F 2002/4687* (2013.01)

(58) Field of Classification Search
CPC .. A61F 2/461; A61F 2002/4627; A61F 2/389; A61F 2/30749; A61F 2/4612; A61F 2/4605; A61F 2/4606; A61B 17/1615; A61B 17/1659; A61B 17/1764; A61B 17/1778; A61B 17/1782
See application file for complete search history.

(56) References Cited

U.S. PATENT DOCUMENTS 3,486,505 A    12/1969   Morrison
3,641,590 A     2/1972   Michele
(Continued)

FOREIGN PATENT DOCUMENTS

EP    0179695         3/1989
WO   WO2010039026    4/2010
WO   WO2011044879    4/2011

*Primary Examiner* — Alvin J Stewart
(74) *Attorney, Agent, or Firm* — KDB Firm PLLC

(57) ABSTRACT

Implants include fixation features which slidingly receive fixation elements. The fixation features may be negative or positive features, such as undercut channels or posts. Examples include unicompartmental tibial trays having a ridge protruding from the bone-facing side, an undercut channel formed within the ridge. Instruments are disclosed for preparing a ridge-receiving feature in bone.

15 Claims, 17 Drawing Sheets

Related U.S. Application Data

(60) Provisional application No. 62/467,083, filed on Mar. 3, 2017.

(51) Int. Cl.
*A61B 17/17* (2006.01)
*A61B 17/16* (2006.01)
*A61F 2/30* (2006.01)
*A61B 90/00* (2016.01)

(56) References Cited

U.S. PATENT DOCUMENTS

| | | |
|---|---|---|
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |
| 4,260,005 A | 4/1981 | Stencel |
| 4,349,955 A | 9/1982 | Keen |
| 4,355,429 A | 10/1982 | Mittelmeier |
| 4,454,875 A | 6/1984 | Pratt |
| 4,484,570 A | 11/1984 | Sutter |
| 4,501,269 A | 2/1985 | Bagby |
| D281,814 S | 12/1985 | Pratt |
| 4,570,623 A | 2/1986 | Ellison |
| 4,611,581 A | 9/1986 | Steffee |
| 4,642,869 A | 2/1987 | Muller |
| 4,681,589 A | 7/1987 | Tronzo |
| 4,716,893 A | 1/1988 | Fischer |
| 4,743,256 A | 5/1988 | Brantigan |
| 4,743,262 A | 5/1988 | Tronzo |
| 4,764,067 A | 8/1988 | Kawashima |
| 4,820,305 A | 4/1989 | Harms |
| 4,834,757 A | 5/1989 | Brantigan |
| 4,838,891 A | 6/1989 | Branemark |
| 4,848,328 A | 7/1989 | Laboureau |
| 4,865,607 A | 9/1989 | Witzel |
| 4,874,389 A | 10/1989 | Downey |
| 4,930,962 A | 6/1990 | Reynolds |
| 4,946,378 A | 8/1990 | Hirayama |
| 4,957,496 A | 9/1990 | Schmidt |
| 5,002,576 A | 3/1991 | Fuhrmann |
| 5,019,103 A | 5/1991 | Van Zile |
| 5,053,038 A | 10/1991 | Sheehan |
| 5,074,880 A | 12/1991 | Mansat |
| 5,147,361 A | 9/1992 | Ojima |
| 5,163,960 A | 11/1992 | Bonutti |
| 5,192,324 A | 3/1993 | Kenna |
| 5,192,327 A | 3/1993 | Brantigan |
| 5,306,309 A | 4/1994 | Wagner |
| 5,314,477 A | 5/1994 | Marnay |
| 5,352,229 A | 10/1994 | Goble |
| 5,366,479 A | 11/1994 | McGarry |
| 5,431,658 A | 7/1995 | Moskovich |
| 5,443,515 A | 8/1995 | Cohen |
| 5,449,359 A | 9/1995 | Groiso |
| 5,454,814 A | 10/1995 | Comte |
| D364,462 S | 11/1995 | Michelson |
| 5,507,816 A | 4/1996 | Bullivant |
| 5,514,180 A | 5/1996 | Heggeness |
| D378,409 S | 3/1997 | Michelson |
| 5,609,635 A | 3/1997 | Michelson |
| 5,658,337 A | 8/1997 | Kohrs |
| 5,660,188 A | 8/1997 | Groiso |
| 5,683,394 A | 11/1997 | Rinner |
| 5,702,449 A | 12/1997 | McKay |
| 5,709,683 A | 1/1998 | Bagby |
| 5,713,899 A | 2/1998 | Marnay |
| 5,769,852 A | 6/1998 | Brønemark |
| 5,772,661 A | 6/1998 | Michelson |
| 5,776,199 A | 7/1998 | Michelson |
| 5,776,202 A | 7/1998 | Copf |
| 5,788,701 A | 8/1998 | McCue |
| 5,800,550 A | 9/1998 | Sertich |
| 5,853,414 A | 12/1998 | Groiso |
| 5,860,973 A | 1/1999 | Michelson |
| 5,885,287 A | 3/1999 | Bagby |
| 5,893,889 A | 4/1999 | Harrington |
| 5,893,890 A | 4/1999 | Pisharodi |
| 5,947,999 A | 9/1999 | Groiso |
| 5,993,476 A | 11/1999 | Groiso |
| 6,039,762 A | 3/2000 | McKay |
| 6,059,787 A | 5/2000 | Allen |
| 6,063,121 A | 5/2000 | Xavier |
| 6,080,155 A | 6/2000 | Michelson |
| 6,096,080 A | 8/2000 | Nicholson |
| 6,102,949 A | 8/2000 | Biedermann |
| 6,102,954 A | 8/2000 | Albrektsson |
| 6,113,638 A | 9/2000 | Williams |
| 6,120,503 A | 9/2000 | Michelson |
| 6,136,001 A | 10/2000 | Michelson |
| 6,159,214 A | 12/2000 | Michelson |
| 6,224,607 B1 | 5/2001 | Michelson |
| 6,235,059 B1 | 5/2001 | Benezech |
| 6,241,769 B1 | 6/2001 | Nicholson |
| 6,241,770 B1 | 6/2001 | Michelson |
| 6,270,498 B1 | 8/2001 | Michelson |
| 6,299,613 B1 | 10/2001 | Ogilvie |
| 6,302,914 B1 | 10/2001 | Michelson |
| 6,309,421 B1 | 10/2001 | Pisharodi |
| 6,325,805 B1 | 12/2001 | Ogilvie |
| 6,336,928 B1 | 1/2002 | Guerin |
| 6,364,880 B1 | 4/2002 | Michelson |
| 6,402,785 B1 | 6/2002 | Zdeblick |
| 6,413,278 B1 | 7/2002 | Marchosky |
| 6,432,107 B1 | 8/2002 | Ferree |
| 6,436,098 B1 | 8/2002 | Michelson |
| 6,447,524 B1 | 9/2002 | Knodel |
| 6,447,544 B1 | 9/2002 | Michelson |
| 6,447,546 B1 | 9/2002 | Bramlet |
| 6,458,159 B1 | 10/2002 | Thalgott |
| 6,478,800 B1 | 11/2002 | Fraser |
| 6,485,517 B1 | 11/2002 | Michelson |
| 6,506,216 B1 | 1/2003 | McCue |
| 6,537,320 B1 | 3/2003 | Michelson |
| 6,558,423 B1 | 5/2003 | Michelson |
| 6,558,424 B2 | 5/2003 | Thalgott |
| 6,582,468 B1 | 6/2003 | Gauchet |
| 6,599,294 B2 | 7/2003 | Fuss |
| 6,610,093 B1 | 8/2003 | Pisharodi |
| 6,620,198 B2 | 9/2003 | Burstein |
| 6,652,533 B2 | 11/2003 | O'Neil |
| 6,679,887 B2 | 1/2004 | Nicholson |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,746,450 B1 | 6/2004 | Wall |
| 6,755,841 B2 | 6/2004 | Fraser |
| 6,767,356 B2 | 7/2004 | Kanner |
| 6,767,367 B1 | 7/2004 | Michelson |
| 6,770,074 B2 | 8/2004 | Michelson |
| 6,770,096 B2 | 8/2004 | Bolger |
| 6,773,437 B2 | 8/2004 | Ogilvie |
| 6,800,093 B2 | 10/2004 | Nicholson |
| 6,802,863 B2 | 10/2004 | Lawson |
| 6,827,740 B1 | 12/2004 | Michelson |
| 6,835,208 B2 | 12/2004 | Marchosky |
| 6,849,093 B2 | 2/2005 | Michelson |
| 6,875,213 B2 | 4/2005 | Michelson |
| 6,923,810 B1 | 8/2005 | Michelson |
| 6,923,830 B2 | 8/2005 | Michelson |
| 6,926,718 B1 | 8/2005 | Michelson |
| 6,942,698 B1 | 9/2005 | Jackson |
| 6,969,390 B2 | 11/2005 | Michelson |
| 6,972,035 B2 | 12/2005 | Michelson |
| 6,981,975 B2 | 1/2006 | Michelson |
| 6,989,031 B2 | 1/2006 | Michelson |
| 7,033,394 B2 | 4/2006 | Michelson |

(56) References Cited

U.S. PATENT DOCUMENTS

| | | |
|---|---|---|
| 7,041,135 B2 | 5/2006 | Michelson |
| 7,044,972 B2 | 5/2006 | Mathys, Jr. et al. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 | 6/2006 | Fraser |
| 7,066,961 B2 | 6/2006 | Michelson |
| 7,083,623 B2 | 8/2006 | Michelson |
| 7,083,652 B2 | 8/2006 | McCue |
| 7,087,082 B2 | 8/2006 | Paul |
| 7,112,206 B2 | 9/2006 | Michelson |
| 7,115,146 B2 | 10/2006 | Boyer, II |
| 7,118,580 B1 | 10/2006 | Beyersdorff |
| 7,128,761 B2 | 10/2006 | Kuras |
| 7,163,560 B2 | 1/2007 | Mason |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,101 B2 | 6/2007 | Berry |
| 7,235,105 B2 | 6/2007 | Jackson |
| 7,238,203 B2 | 7/2007 | Bagga |
| 7,255,698 B2 | 8/2007 | Michelson |
| 7,320,707 B2 | 1/2008 | Zucherman |
| 7,326,248 B2 | 2/2008 | Michelson |
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,462,196 B2 | 12/2008 | Fraser |
| 7,481,830 B2 | 1/2009 | Wall |
| 7,481,832 B1 | 1/2009 | Meridew |
| D586,915 S | 2/2009 | Grim |
| 7,491,205 B1 | 2/2009 | Michelson |
| 7,503,933 B2 | 3/2009 | Michelson |
| 7,503,934 B2 | 3/2009 | Eisermann |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,611,538 B2 | 11/2009 | Belliard |
| 7,658,766 B2 | 2/2010 | Melkent |
| 7,695,516 B2 | 4/2010 | Zeegers |
| 7,749,271 B2 | 7/2010 | Fischer |
| 7,763,076 B2 | 7/2010 | Navarro |
| 7,780,676 B2 | 8/2010 | Lakin |
| 7,837,732 B2 | 11/2010 | Zucherman |
| 7,850,791 B2 | 12/2010 | Quadakkers |
| 7,883,510 B2 | 2/2011 | Kim |
| 7,887,563 B2 | 2/2011 | Cummins |
| 7,896,919 B2 | 3/2011 | Belliard |
| 7,909,871 B2 | 3/2011 | Abdou |
| 7,918,891 B1 | 4/2011 | Curran |
| 7,966,799 B2 | 6/2011 | Morgan |
| 8,021,403 B2 | 9/2011 | Wall |
| 8,034,076 B2 | 10/2011 | Criscuolo |
| 8,062,297 B2 | 11/2011 | Faillace |
| 8,100,972 B1 | 1/2012 | Bruffey |
| 8,100,974 B2 | 1/2012 | Duggal |
| 8,105,389 B2 | 1/2012 | Berelsman |
| 8,123,757 B2 | 2/2012 | Zalenski |
| 8,133,283 B2 | 3/2012 | Wilson |
| 8,157,865 B2 | 4/2012 | Hochschuler |
| 8,287,572 B2 | 10/2012 | Bae |
| 8,491,598 B2 | 7/2013 | Crook |
| 8,500,747 B2 | 8/2013 | DeRidder et al. |
| 8,636,191 B2 | 1/2014 | Meagher |
| 8,747,412 B2 | 6/2014 | Bae |
| 8,808,294 B2 | 8/2014 | Fox |
| 9,254,130 B2 | 2/2016 | Hollis |
| 9,480,511 B2 | 11/2016 | Butters |
| 9,592,131 B2 | 3/2017 | Sandstrom |
| 9,615,856 B2 | 4/2017 | Arnett |
| 9,788,968 B2 | 10/2017 | Bae |
| 9,925,051 B2 | 3/2018 | Bae |
| 9,968,464 B2 | 5/2018 | Tanaka |
| 10,238,382 B2 | 3/2019 | Terrill |
| 10,238,426 B2 | 3/2019 | Butters |
| 10,245,090 B2 | 4/2019 | Hollis |
| 10,342,667 B2 | 7/2019 | Bae |
| 10,390,955 B2 | 8/2019 | Bae |
| 10,456,272 B2 | 10/2019 | Su |
| 2001/0000532 A1 | 4/2001 | Michelson |
| 2001/0010001 A1 | 7/2001 | Michelson |
| 2001/0010002 A1 | 7/2001 | Michelson |
| 2001/0010020 A1 | 7/2001 | Michelson |
| 2001/0037154 A1 | 11/2001 | Martin |
| 2001/0047207 A1 | 11/2001 | Michelson |
| 2001/0047208 A1 | 11/2001 | Michelson |
| 2002/0004683 A1 | 1/2002 | Michelson |
| 2002/0035400 A1 | 3/2002 | Bryan |
| 2002/0049447 A1 | 4/2002 | Li |
| 2002/0091390 A1 | 7/2002 | Michelson |
| 2002/0095155 A1 | 7/2002 | Michelson |
| 2002/0099376 A1 | 7/2002 | Michelson |
| 2002/0099378 A1 | 7/2002 | Michelson |
| 2002/0116065 A1 | 8/2002 | Jackson |
| 2002/0116165 A1 | 8/2002 | El Ghoroury |
| 2002/0147454 A1 | 10/2002 | Neto |
| 2002/0147499 A1 | 10/2002 | Shea |
| 2002/0161443 A1 | 10/2002 | Michelson |
| 2002/0165613 A1 | 11/2002 | Lin |
| 2003/0023307 A1 | 1/2003 | Michelson |
| 2003/0045940 A1 | 3/2003 | Eberlein |
| 2003/0060884 A1 | 3/2003 | Fell |
| 2003/0120344 A1 | 6/2003 | Michelson |
| 2003/0149483 A1 | 8/2003 | Michelson |
| 2003/0158553 A1 | 8/2003 | Michelson |
| 2003/0195517 A1 | 10/2003 | Michelson |
| 2003/0195561 A1 | 10/2003 | Carley |
| 2003/0195632 A1 | 10/2003 | Foley |
| 2004/0030336 A1 | 2/2004 | Khanna |
| 2004/0030339 A1 | 2/2004 | Wack |
| 2004/0064185 A1 | 4/2004 | Michelson |
| 2004/0073315 A1 | 4/2004 | Justin |
| 2004/0083005 A1 | 4/2004 | Jacobsson |
| 2004/0117018 A1 | 6/2004 | Michelson |
| 2004/0122518 A1 | 6/2004 | Rhoda |
| 2004/0133203 A1 | 7/2004 | Young |
| 2004/0148028 A1 | 7/2004 | Ferree |
| 2004/0176853 A1 | 9/2004 | Sennett |
| 2004/0210313 A1 | 10/2004 | Michelson |
| 2004/0210314 A1 | 10/2004 | Michelson |
| 2004/0215203 A1 | 10/2004 | Michelson |
| 2004/0220668 A1 | 11/2004 | Eisermann |
| 2004/0220670 A1 | 11/2004 | Eisermann |
| 2004/0225295 A1 | 11/2004 | Zubok |
| 2004/0230308 A1 | 11/2004 | Michelson |
| 2004/0249388 A1 | 12/2004 | Michelson |
| 2004/0254581 A1 | 12/2004 | Leclair |
| 2004/0254644 A1 | 12/2004 | Taylor |
| 2004/0260286 A1 | 12/2004 | Ferree |
| 2005/0004672 A1 | 1/2005 | Pafford |
| 2005/0014919 A1 | 1/2005 | Hatakeyama |
| 2005/0027300 A1 | 2/2005 | Hawkins |
| 2005/0038512 A1 | 2/2005 | Michelson |
| 2005/0038513 A1 | 2/2005 | Michelson |
| 2005/0043802 A1 | 2/2005 | Eisermann |
| 2005/0049600 A1 | 3/2005 | Groiso |
| 2005/0055031 A1 | 3/2005 | Lim |
| 2005/0113842 A1 | 5/2005 | Bertagnoli |
| 2005/0125065 A1 | 6/2005 | Zucherman |
| 2005/0131545 A1 | 6/2005 | Chervitz |
| 2005/0143747 A1 | 6/2005 | Zubok |
| 2005/0149192 A1 | 7/2005 | Zucherman |
| 2005/0165408 A1 | 7/2005 | Puno |
| 2005/0171550 A1 | 8/2005 | Marik |
| 2005/0171606 A1 | 8/2005 | Michelson |
| 2005/0171607 A1 | 8/2005 | Michelson |
| 2005/0177239 A1 | 8/2005 | Steinberg |
| 2005/0187629 A1 | 8/2005 | Michelson |

(56) References Cited

U.S. PATENT DOCUMENTS

| | | |
|---|---|---|
| 2005/0192586 A1 | 9/2005 | Zucherman |
| 2005/0216089 A1 | 9/2005 | Michelson |
| 2005/0234555 A1 | 10/2005 | Sutton |
| 2005/0273108 A1 | 12/2005 | Groiso |
| 2006/0004453 A1 | 1/2006 | Bartish |
| 2006/0058802 A1 | 3/2006 | Kofoed |
| 2006/0074421 A1 | 4/2006 | Bickley |
| 2006/0079961 A1 | 4/2006 | Michelson |
| 2006/0085071 A1 | 4/2006 | Lechmann |
| 2006/0095136 A1 | 5/2006 | McLuen |
| 2006/0111787 A1 | 5/2006 | Bailie |
| 2006/0116769 A1 | 6/2006 | Marnay |
| 2006/0122702 A1 | 6/2006 | Michelson |
| 2006/0129238 A1 | 6/2006 | Paltzer |
| 2006/0136061 A1 | 6/2006 | Navarro |
| 2006/0142860 A1 | 6/2006 | Navarro |
| 2006/0149377 A1 | 7/2006 | Navarro |
| 2006/0149384 A1 | 7/2006 | Navarro |
| 2006/0167461 A1 | 7/2006 | Hawkins |
| 2006/0178745 A1 | 8/2006 | Bartish |
| 2006/0195097 A1 | 8/2006 | Evans |
| 2006/0195191 A1 | 8/2006 | Sweeney |
| 2006/0212123 A1 | 9/2006 | Lechmann |
| 2006/0241641 A1 | 10/2006 | Albans |
| 2006/0259143 A1 | 11/2006 | Navarro |
| 2006/0259145 A1 | 11/2006 | Navarro |
| 2007/0010822 A1 | 1/2007 | Zalenski |
| 2007/0010890 A1 | 1/2007 | Collazo |
| 2007/0050032 A1 | 3/2007 | Gittings |
| 2007/0050033 A1 | 3/2007 | Reo |
| 2007/0055376 A1 | 3/2007 | Michelson |
| 2007/0055381 A1 | 3/2007 | Berelsman |
| 2007/0073404 A1 | 3/2007 | Rashbaum |
| 2007/0093839 A1 | 4/2007 | Beckendorf |
| 2007/0106388 A1 | 5/2007 | Michelson |
| 2007/0118132 A1 | 5/2007 | Culbert |
| 2007/0123903 A1 | 5/2007 | Raymond |
| 2007/0142922 A1 | 6/2007 | Lewis |
| 2007/0179621 A1 | 8/2007 | McClellan |
| 2007/0185375 A1 | 8/2007 | Stad |
| 2007/0225812 A1 | 9/2007 | Gill |
| 2007/0233244 A1 | 10/2007 | Lopez |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0051901 A1 | 2/2008 | de Villiers |
| 2008/0051902 A1 | 2/2008 | Dwyer |
| 2008/0103598 A1 | 5/2008 | Trudeau |
| 2008/0108997 A1 | 5/2008 | Berrevoets |
| 2008/0132949 A1 | 6/2008 | Aferzon |
| 2008/0133017 A1 | 6/2008 | Beyar |
| 2008/0140208 A1 | 6/2008 | Zucherman |
| 2008/0147203 A1 | 6/2008 | Cronin |
| 2008/0154377 A1 | 6/2008 | Voellmicke |
| 2008/0167721 A1 | 7/2008 | Bao |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0269764 A1 | 10/2008 | Blain |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0018560 A1 | 1/2009 | Mayer |
| 2009/0048604 A1 | 2/2009 | Milz |
| 2009/0062921 A1 | 3/2009 | Michelson |
| 2009/0088849 A1 | 4/2009 | Armstrong |
| 2009/0099601 A1 | 4/2009 | Aferzon |
| 2009/0099602 A1 | 4/2009 | Aflatoon |
| 2009/0164020 A1 | 6/2009 | Janowski |
| 2009/0209967 A1 | 8/2009 | Evans |
| 2009/0240333 A1 | 9/2009 | Trudeau |
| 2010/0004747 A1 | 1/2010 | Lin |
| 2010/0069958 A1 | 3/2010 | Sullivan |
| 2010/0076441 A1 | 3/2010 | May |
| 2010/0185287 A1 | 7/2010 | Allard |
| 2010/0201739 A1 | 8/2010 | Yamaguchi |
| 2010/0204739 A1 | 8/2010 | Bae |
| 2010/0217395 A1 | 8/2010 | Bertagnoli |
| 2010/0268238 A1 | 10/2010 | Sikora |
| 2011/0022176 A1 | 1/2011 | Zucherman |
| 2011/0054620 A1 | 3/2011 | Reo |
| 2011/0098819 A1 | 4/2011 | Eisermann |
| 2011/0106260 A1 | 5/2011 | Laurence |
| 2011/0160766 A1 | 6/2011 | Hendren |
| 2011/0160866 A1 | 6/2011 | Laurence |
| 2011/0166608 A1 | 7/2011 | Duggal |
| 2012/0083788 A1 | 4/2012 | Blakemore |
| 2012/0215315 A1 | 8/2012 | Hochschuler |
| 2012/0253406 A1 | 10/2012 | Bae |
| 2012/0259335 A1 | 10/2012 | Scifert et al. |
| 2012/0265259 A1 | 10/2012 | Laposta et al. |
| 2012/0283837 A1 | 11/2012 | Bae et al. |
| 2013/0013006 A1 | 1/2013 | Rashbaum et al. |
| 2014/0039632 A1 | 2/2014 | Hollis |
| 2014/0171952 A1 | 6/2014 | Maxson et al. |
| 2016/0008012 A1 | 1/2016 | Balzarini |
| 2017/0367837 A1 | 12/2017 | Harris, Jr. |
| 2019/0038298 A1 | 2/2019 | Bojarski et al. |
| 2019/0321187 A1 | 10/2019 | Bae et al. |

UNICOMPARTMENTAL KNEE ARTHROPLASTY

CROSS-REFERENCE TO RELATED APPLICATIONS

The present application is a continuation of:

U.S. patent application Ser. No. 15/910,962, entitled UNICOMPARTMENTAL KNEE ARTHROPLASTY, which was filed on Mar. 2, 2018.

U.S. patent application Ser. No. 15/910,962 claims the benefit of:

U.S. Provisional Patent Application No. 62/467,083, entitled UNICOMPARTMENTAL KNEE ARTHROPLASTY, which was filed on Mar. 3, 2017.

The foregoing are incorporated by reference as though set forth herein in their entirety.

TECHNICAL FIELD

The present disclosure relates to arthroplasty. More specifically, the present disclosure is made in the context of unicompartmental knee arthroplasty. Those of skill in the art will appreciate that the disclosed technology is applicable to other types of arthroplasty.

BACKGROUND

Arthroplasty procedures seek to replace a natural joint that has deteriorated in its functionality. Joint resurfacing typically involves removal of at least a portion of a natural articular surface of a bone in order to replace the removed tissue with a prosthesis having an articular surface that replicates at least the removed portion of the natural articular surface. Joint replacement may involve more extensive bone removal and subsequent replacement with a more substantial prosthesis. In this disclosure, remarks about resurfacing are to be considered equally relevant to replacement, and vice versa.

Arthroplasty procedures may involve one or more articular surfaces of a joint. In the knee, for example, the medial femoral condyle, the lateral femoral condyle, the medial tibial condyle, the lateral tibial condyle, the trochlear groove, and/or the patella may be resurfaced or replaced. A procedure may be described as unicondylar if one condyle of the joint is treated, such as the medial tibial condyle. Bicondylar procedures may treat two condyles of a bone, such as the medial and lateral tibial condyles. A procedure may be described as unicompartmental if one compartment of the joint is treated, such as the medial compartment of the knee. Bicompartmental procedures may treat two compartments, such as the medial and lateral compartments of the knee. A procedure may be described as a total joint procedure if most or all opposing articular surfaces of the joint are resurfaced or replaced. A procedure may be described as a hemiarthroplasty procedure if the prosthetic component articulates against an opposing natural articular surface, such as the prosthetic medial tibial component articulating against the natural medial femoral condyle.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

DETAILED DESCRIPTION

Figure 1:
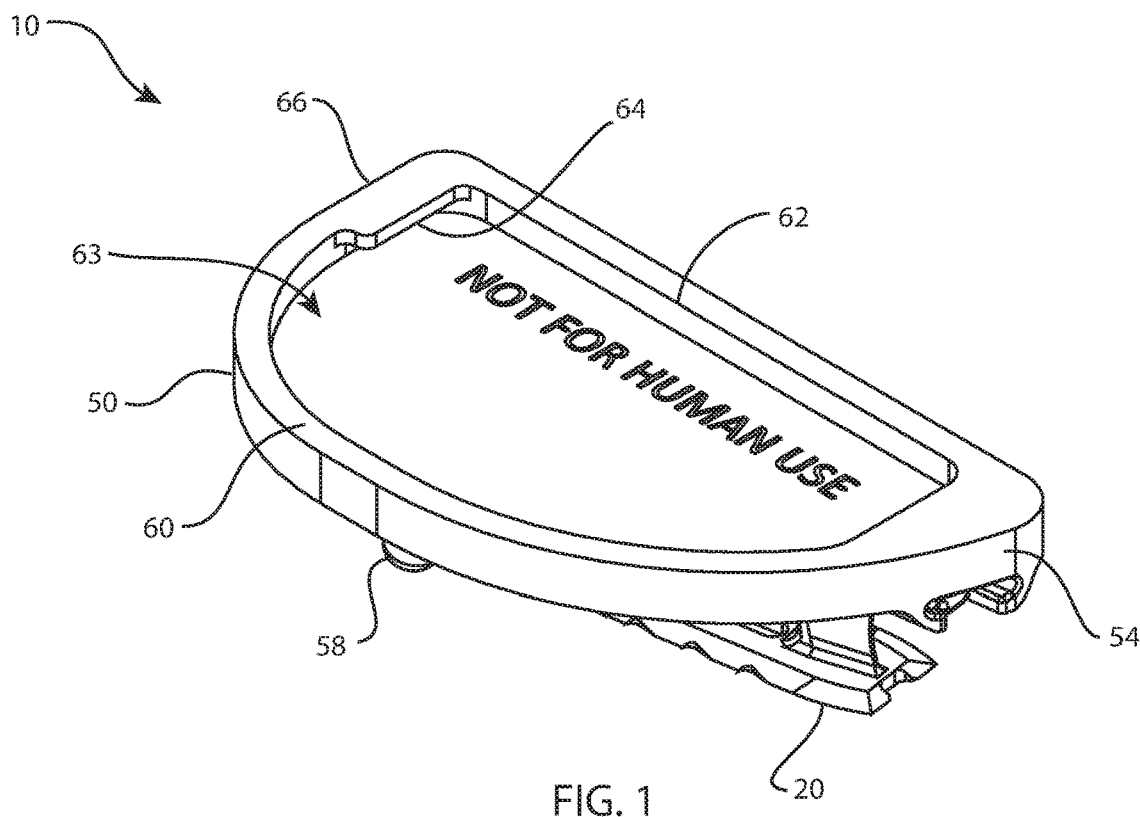
FIG. 1 is a perspective view of a unicompartmental tibial tray and a fixation element.
Figure 2:
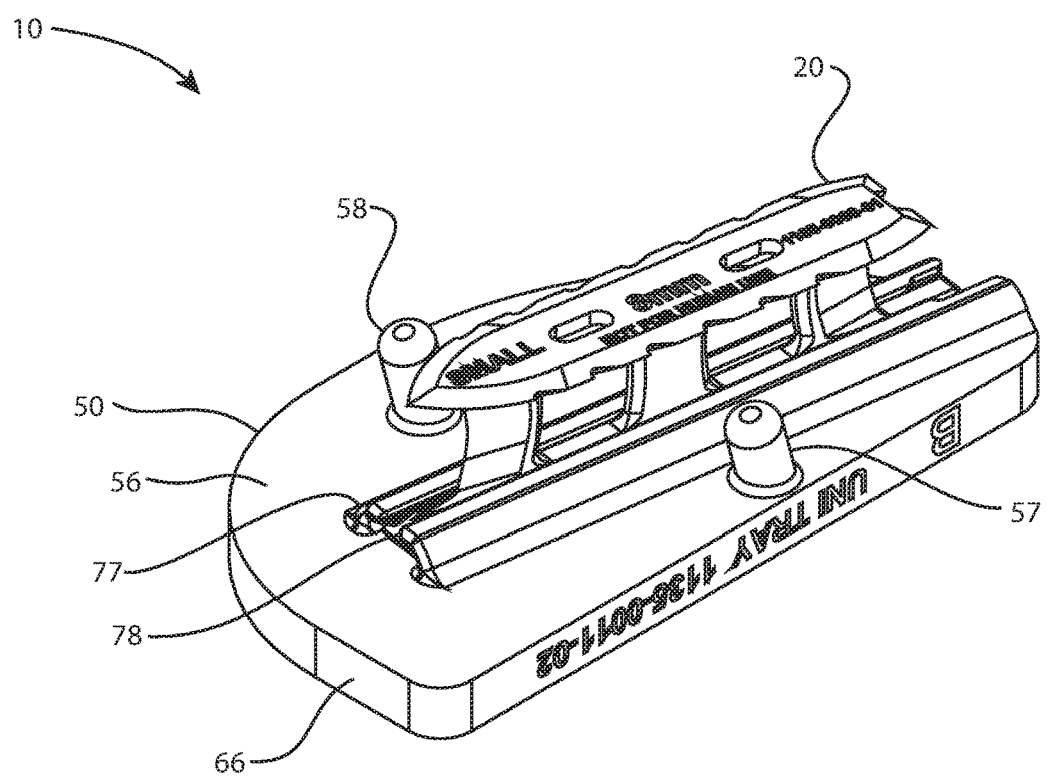
FIG. 2 is another perspective view of the tibial tray and fixation element of FIG. 1 from a different direction.
Figure 3:
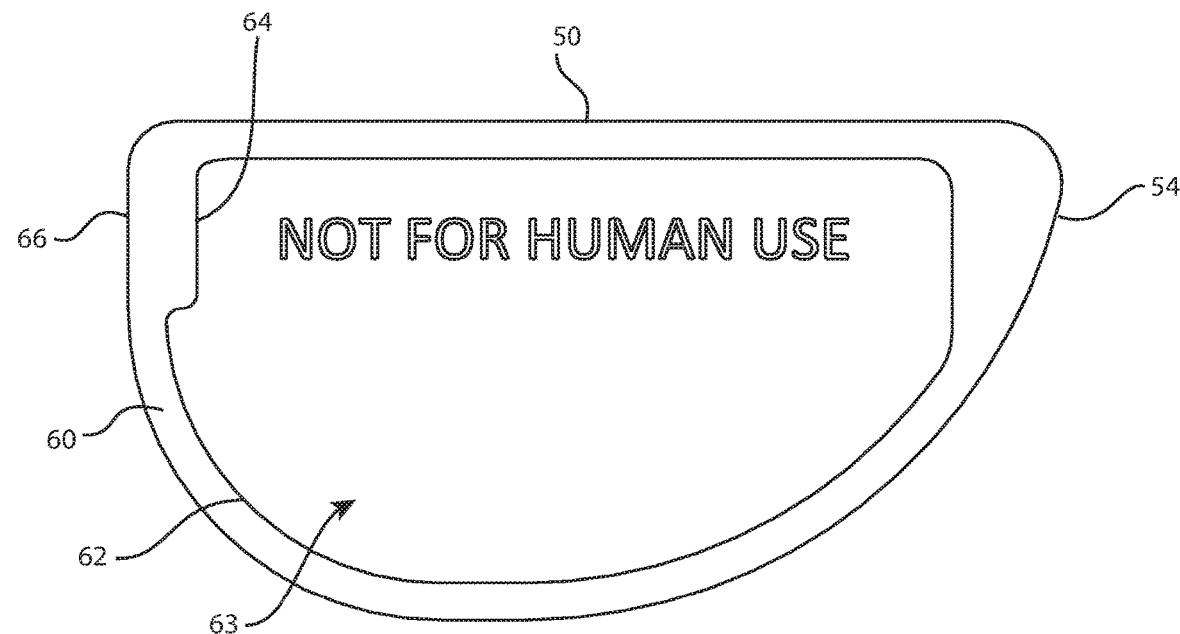
FIG. 3 is a top view of the tibial tray of FIG. 1.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot.

Standard terminology related to knee arthroplasty is employed in this specification with the ordinary and customary meanings. Varus means deviation of the distal part of the leg below the knee inward, resulting in a bowlegged appearance. Valgus means deviation of the distal part of the leg below the knee outward, resulting in a knock-kneed appearance.

Figure 18:
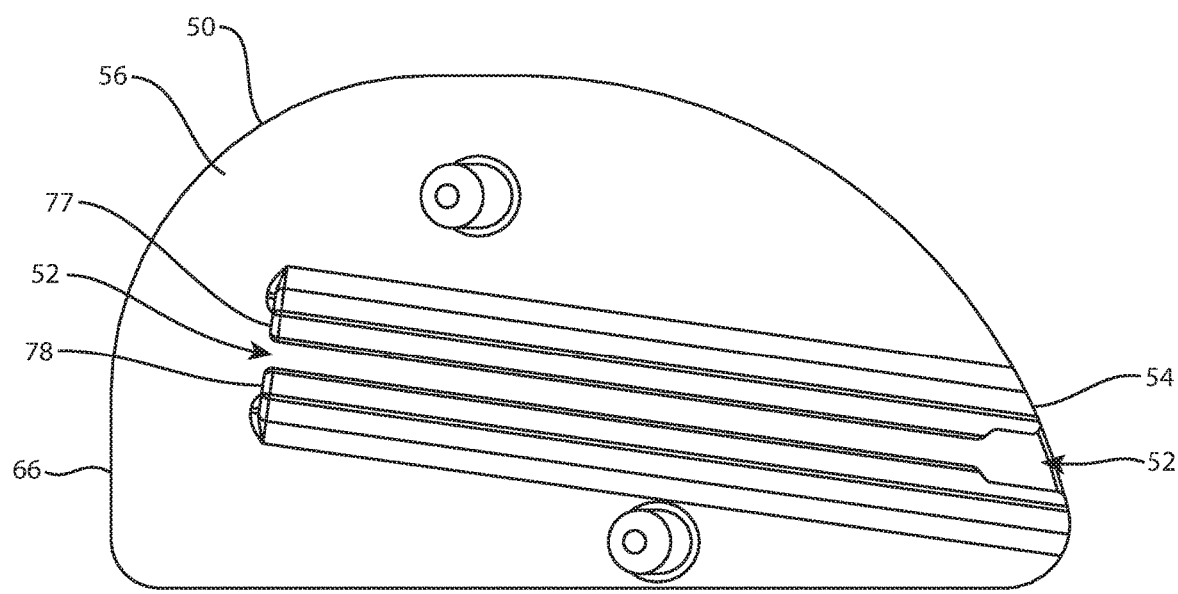
FIG. 18 is a bottom view of the tibial tray of FIG. 1.
Figure 19:
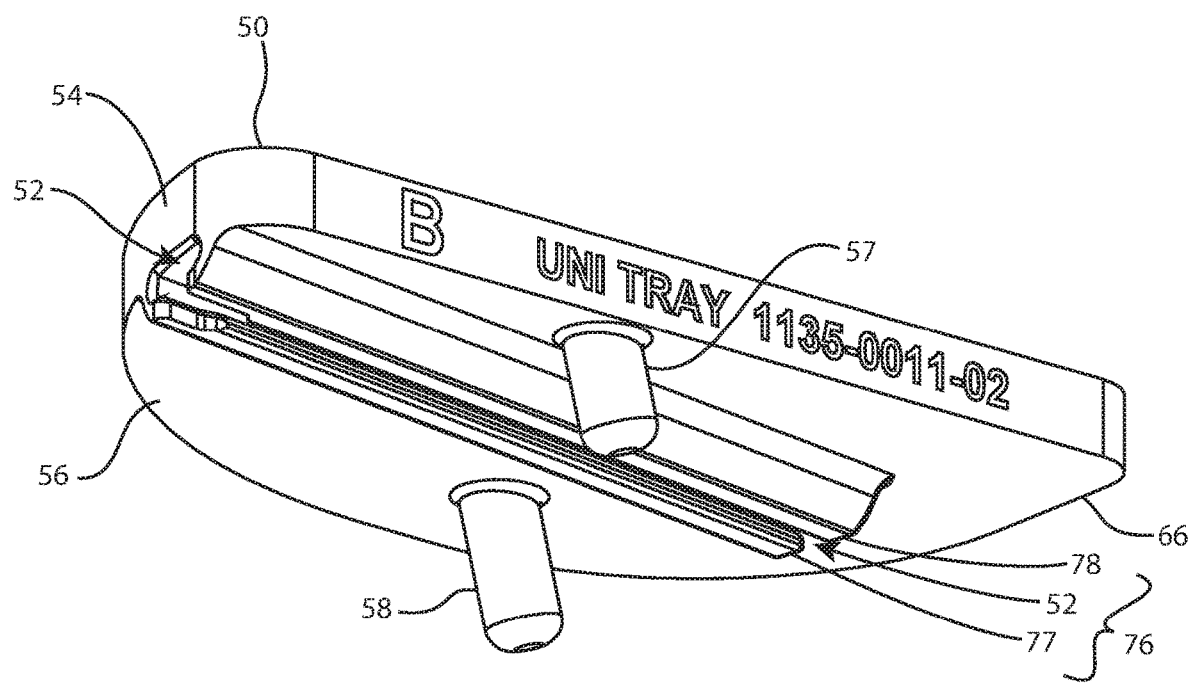
FIG. 19 is a perspective view of the tibial tray of FIG. 1.
Figure 20:
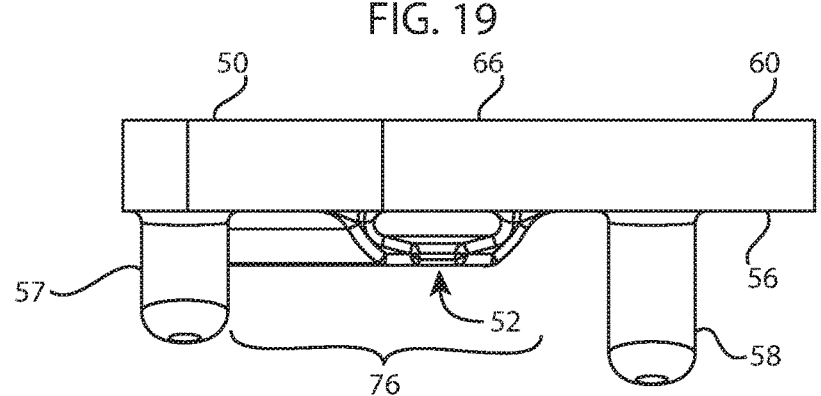
FIG. 20 is left view of the tibial tray of FIG. 1.
Figure 21:
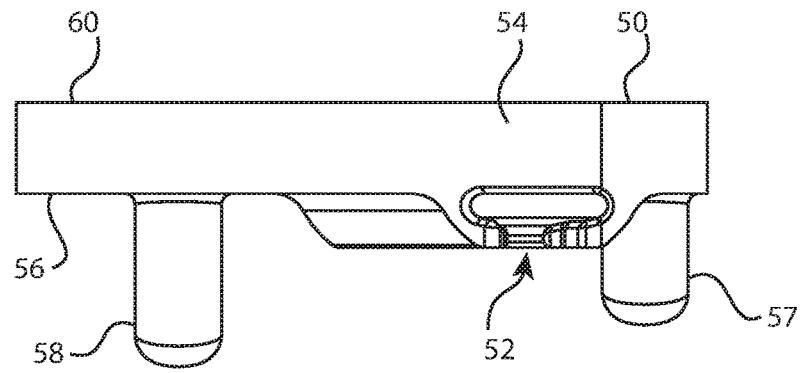
FIG. 21 is a right view of the tibial tray of FIG. 1.
Figure 22:
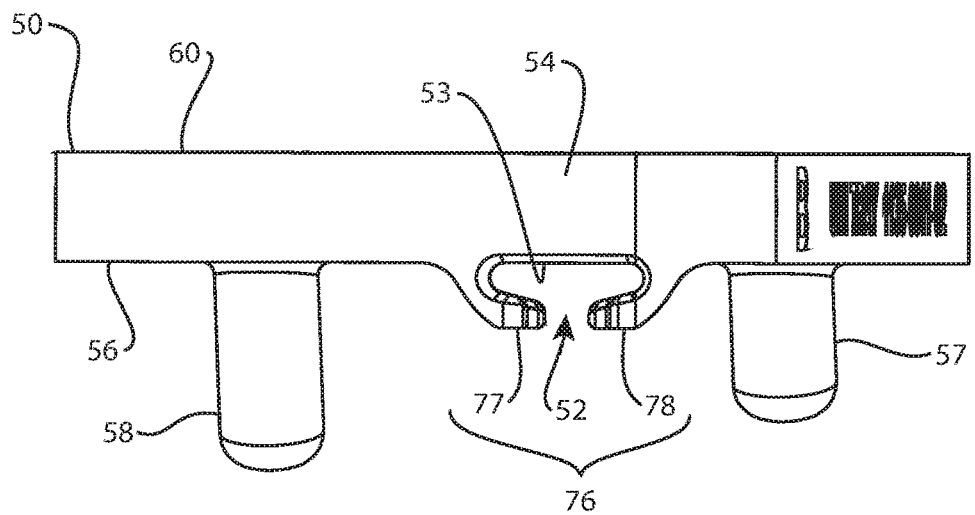
FIG. 22 is another auxiliary view of the tibial tray of FIG. 1 taken along line 10-10 of FIG. 9 parallel to the plane of symmetry of the fixation element.
Figure 23:
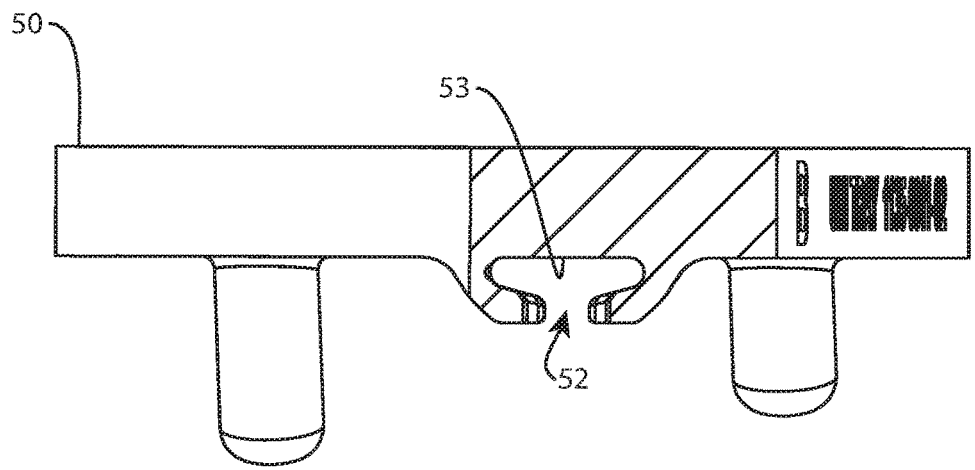
FIG. 23 is a cross sectional view of the tibial tray of FIG. 1 taken along line 11-11 of FIG. 9.
Figure 24:
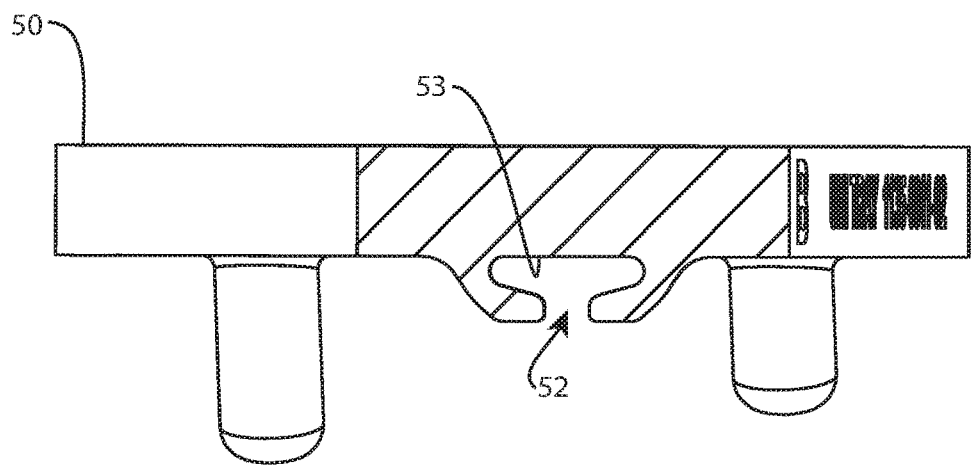
FIG. 24 is a cross sectional view of the tibial tray of FIG. 1 taken along line 12-12 of FIG. 9.
Figure 25:
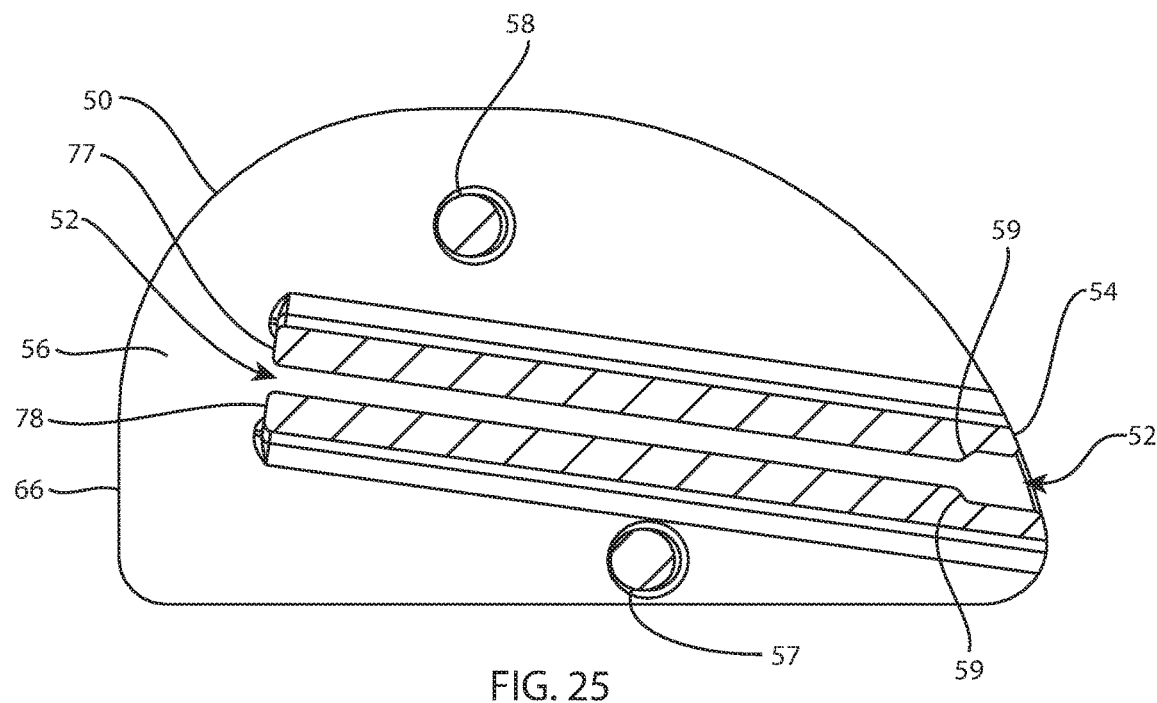
FIG. 25 is a cross sectional view of the tibial tray of FIG. 1 taken along line 17-17 of FIG. 9.

Referring to FIGS. 1-36, a knee tibial prosthesis 10 includes a tibial component 50 and at least one fixation element 20. The tibial component 50 may be referred to as a tibial tray 50. The illustrated tibial component 50 is a unicompartmental tibial component. The tibial prosthesis 10 of FIG. 1 includes one fixation element 20, which may be referred to as an anchor 20. Multiple anchors may be present. The anchor 20 may be inserted from an anterior edge 54 of the tibial tray 50 and may be oriented roughly anterior-posterior, as shown. The anchor 20 may be parallel or angled relative to another anchor (if present) and/or the tray 50. The anchor may also be tilted with respect to the tray 50, for example, tilted medially or laterally. The anchor 20 is inserted into a channel 52 in the tibial tray 50 (FIG. 18). Multiple channels may be present. The channel may be dovetailed as shown; other undercut channel geometries are contemplated, such as T-slots. The channel 52 is shown extending between anterior and posterior edges 54, 66 of the tray 50. In some embodiments, the channel may only open at one of the anterior and posterior edges 54, 66, and may terminate in the main body of the tray 50. In other examples, the channel 52 may be oriented exactly anterior-posterior, exactly medial-lateral, generally medial-lateral, or in another orientation. A channel 52 may open through any perimeter edge of a bone-contacting side 56 of the tray 50.

The anchors in the present disclosure may share some or all of the features of the anchors disclosed in U.S. patent application Ser. No. 12/640,892 to Bae, et al. or U.S. patent application Ser. No. 13/328,592 to Bae, et al., which are incorporated by reference herein in their entirety.

Figure 26:
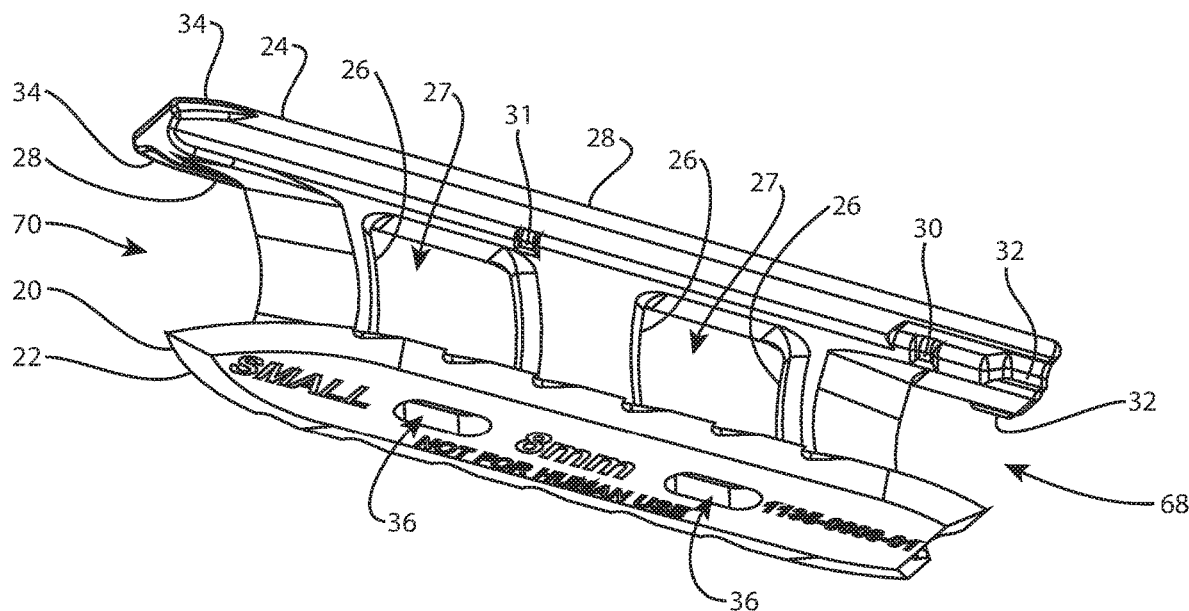
FIG. 26 is a perspective view of the fixation element of FIG. 1.

Referring mainly to FIGS. 26-36, each fixation element or anchor 20 comprises a blade 22 and a rail 24. The blade and rail extend between a leading end 70 and a trailing end 68 of the anchor. The leading end 70 may also be referred to as a distal end 70; the trailing end 68 may also be referred to as a proximal end 68. Supports 26 connect the blade 22 to the rail 24. FIG. 26 illustrates an anchor 20 with three supports 26, although other examples may include any number of supports. The supports 26 define apertures 27 through the anchor 20. In use, the blade 22 and at least a portion of the supports 26 may be inserted into bone which is adjacent to the bone-contacting side 56 of the tray 50. The blade 22 may be pointed, sharpened, and/or serrated, for ease of insertion into bone. The supports 26 may also be sharpened and/or obliquely profiled for ease of insertion into bone. The blade edges may be beveled. The blade 22 may be pierced by one or more apertures 36. Longitudinal edges 28 of the rail may be sized and shaped for complementary engagement with the dovetail channels 52 of the tray 50. In other examples, the rail may be of a complementary size and shape to engage another undercut channel geometry.

Figure 28:
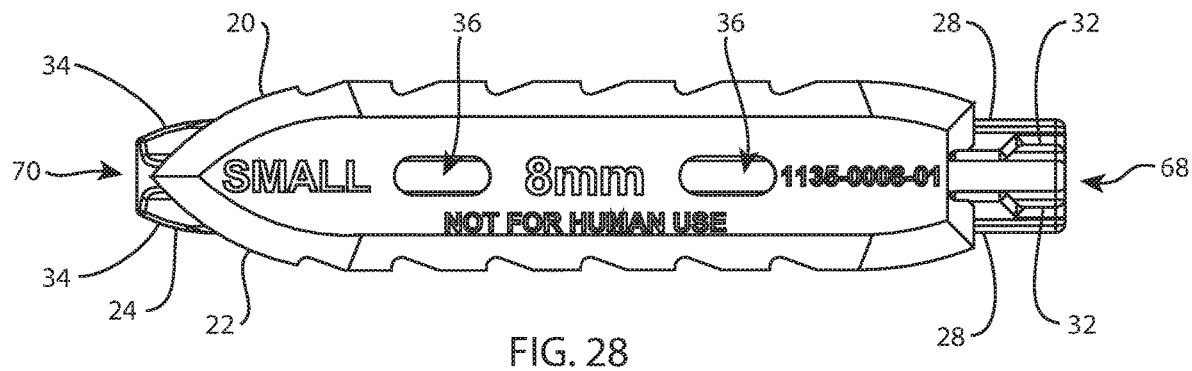
FIG. 28 is a bottom view of the fixation element of FIG. 1.
Figure 29:
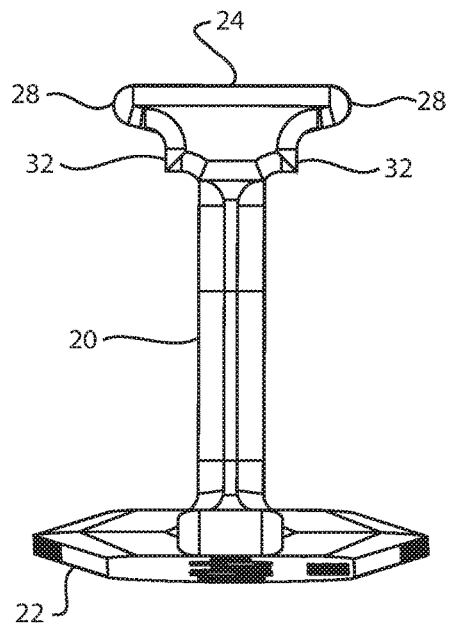
FIG. 29 is a right view of the fixation element of FIG. 1.
Figure 30:
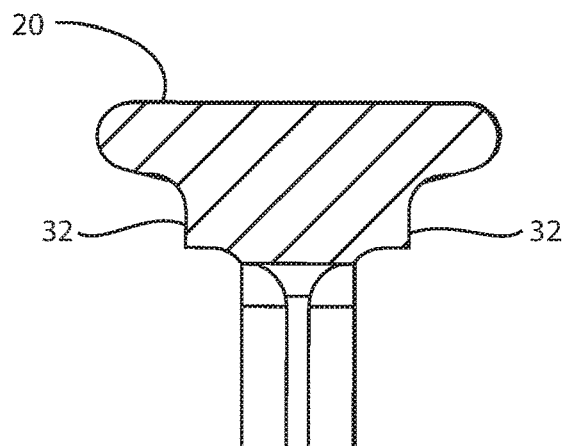
FIG. 30 is a cross sectional view of the fixation element of FIG. 1 taken along line 11-11 of FIG. 9.
Figure 31:
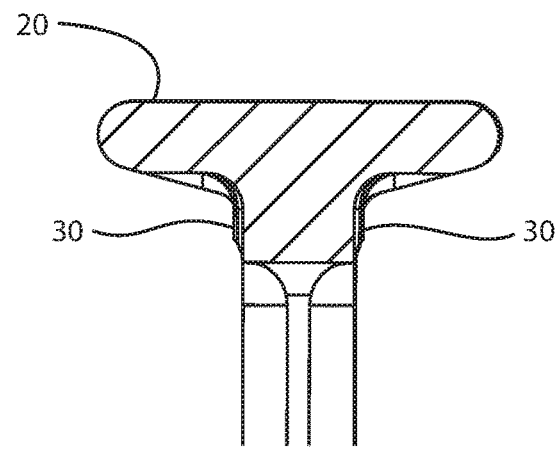
FIG. 31 is a cross sectional view of the fixation element of FIG. 1 taken along line 12-12 of FIG. 9.
Figure 32:
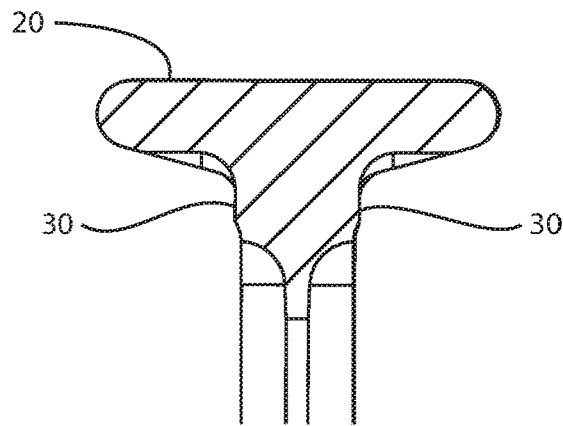
FIG. 32 is a cross sectional view of the fixation element of FIG. 1 taken along line 13-13 of FIG. 9.
Figure 33:
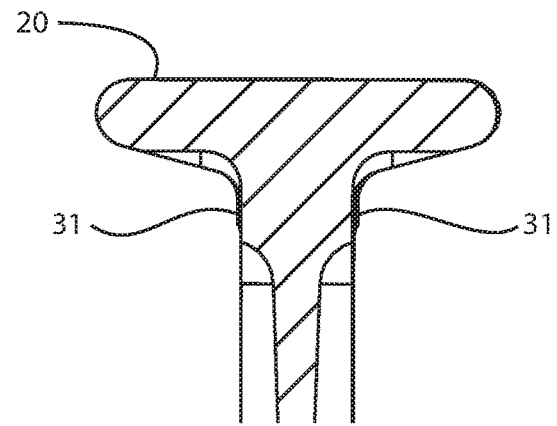
FIG. 33 is a cross sectional view of the fixation element of FIG. 1 taken along line 14-14 of FIG. 9.
Figure 34:
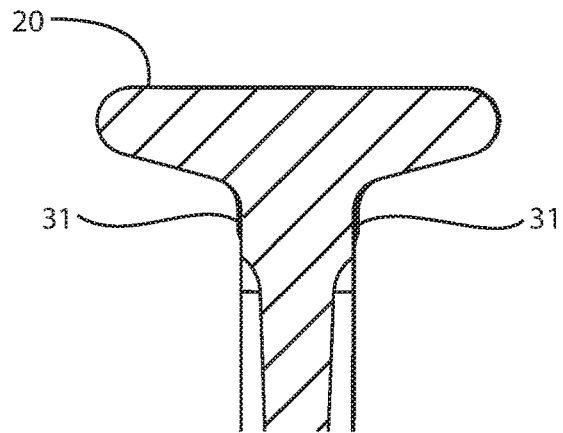
FIG. 34 is a cross sectional view of the fixation element of FIG. 1 taken along line 15-15 of FIG. 9.
Figure 35:
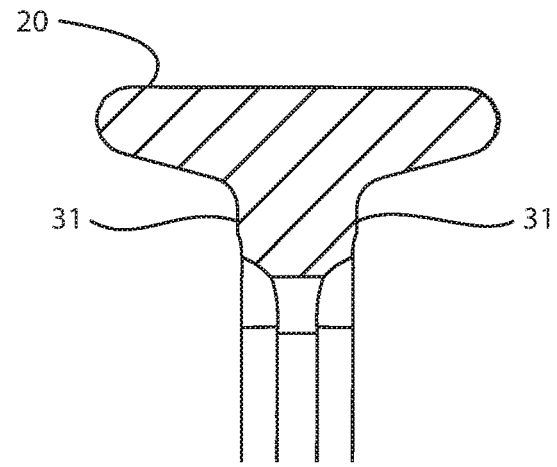
FIG. 35 is a cross sectional view of the fixation element of FIG. 1 taken along line 16-16 of FIG. 9.
Figure 36:
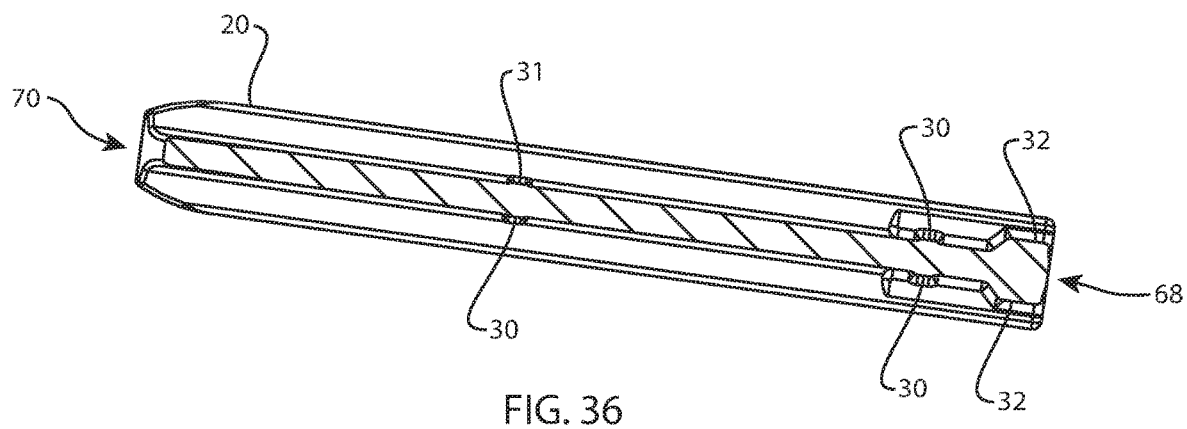
FIG. 36 is a cross sectional view of the fixation element of FIG. 1 taken along line 17-17 of FIG. 9.
Figure 37:
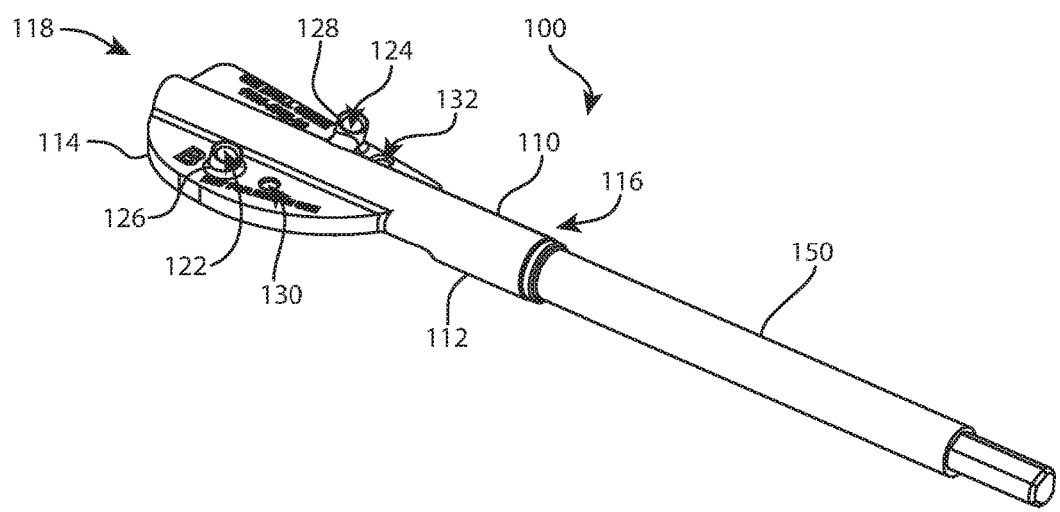
FIG. 37 is a perspective view of a unicondylar drill guide and a drill.
Figure 38:
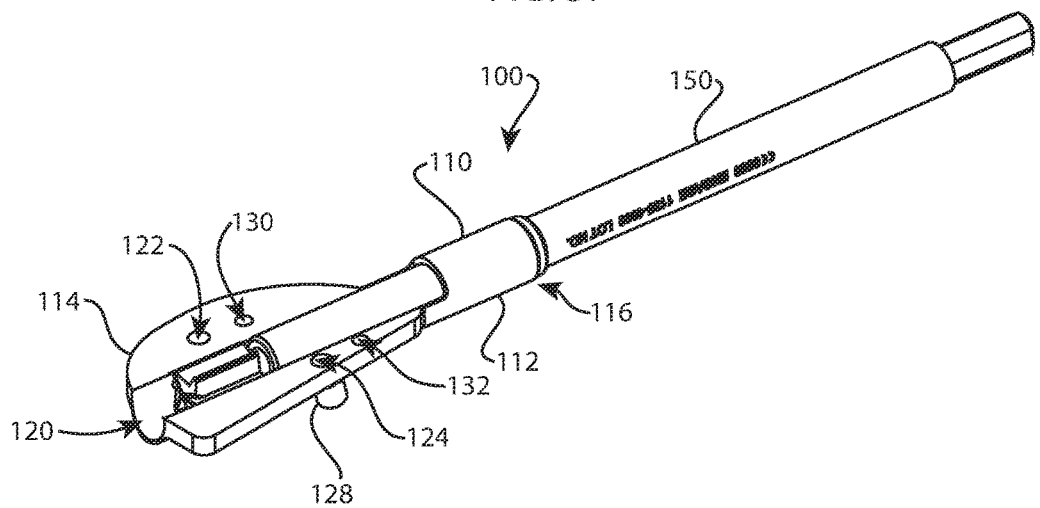
FIG. 38 is another perspective view of the drill guide and drill of FIG. 37.
Figure 39:
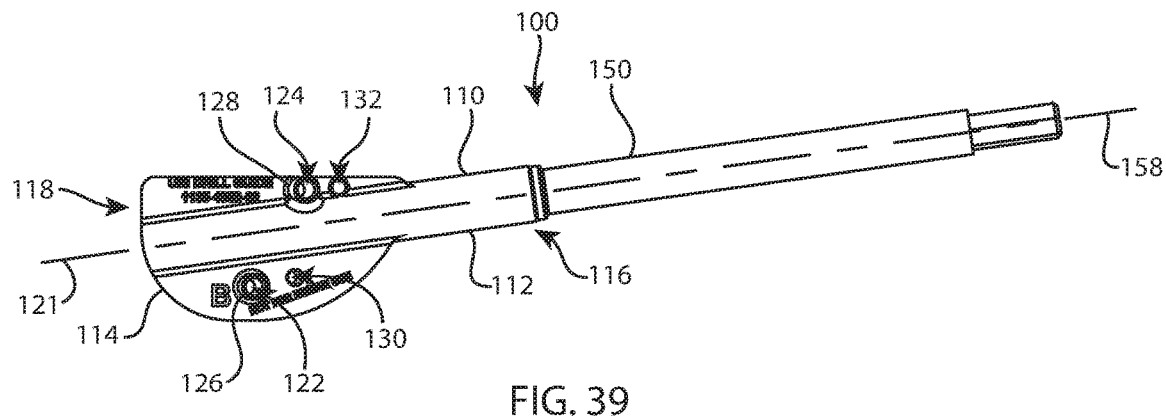
FIG. 39 is a top view of the drill guide and drill of FIG. 37.
Figure 40:
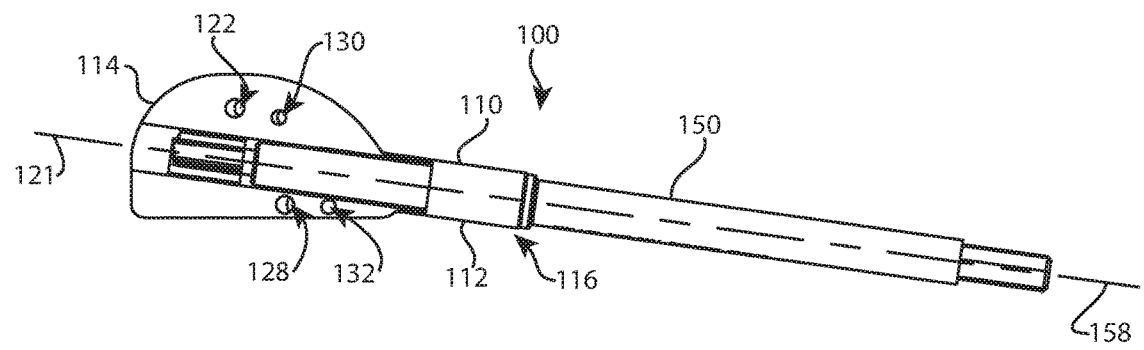
FIG. 40 is a bottom view of the drill guide and drill of FIG. 37.
Figure 41:
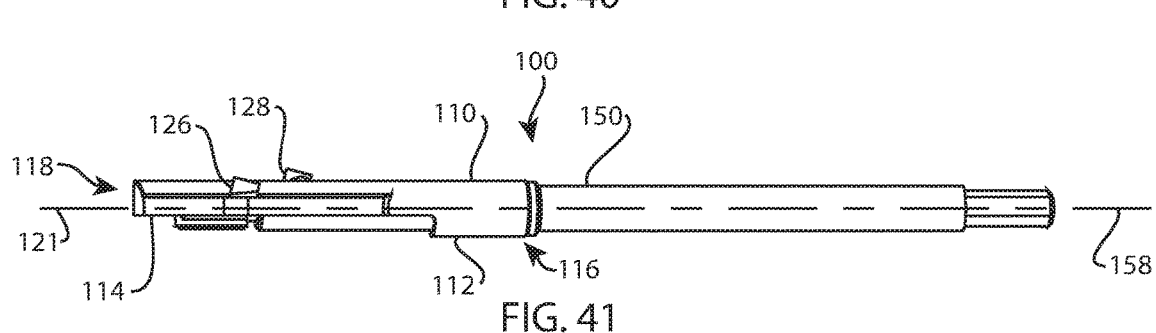
FIG. 41 is a front view of the drill guide and drill of FIG. 37.
Figure 42:
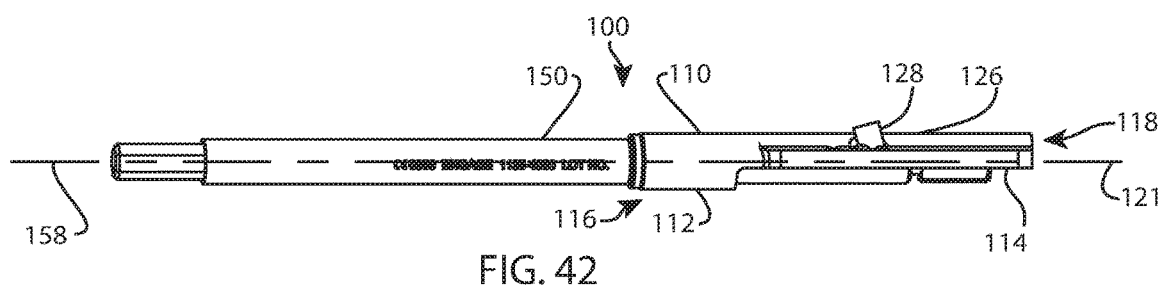
FIG. 42 is a back view of the drill guide and drill of FIG. 37.
Figure 43:
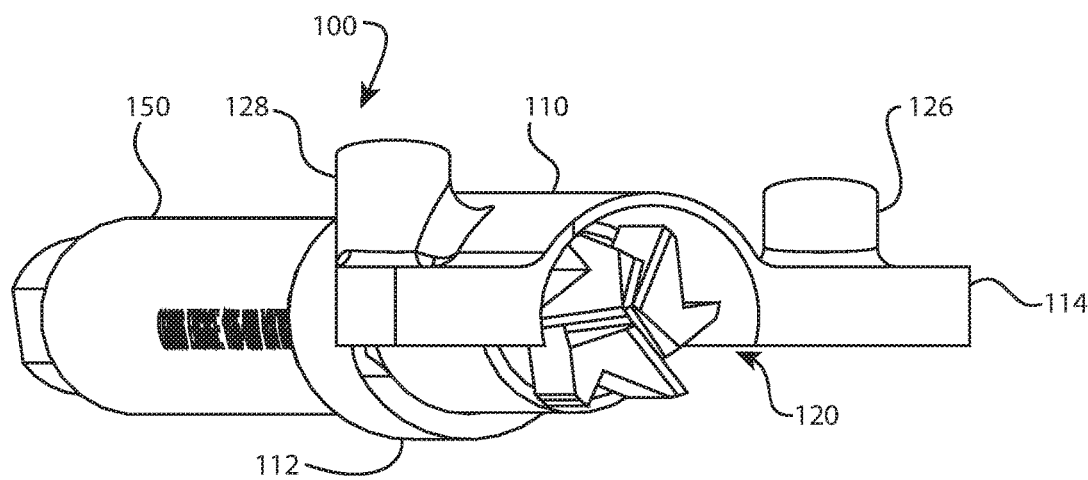
FIG. 43 is a left view of the drill guide and drill of FIG. 37.
Figure 44:
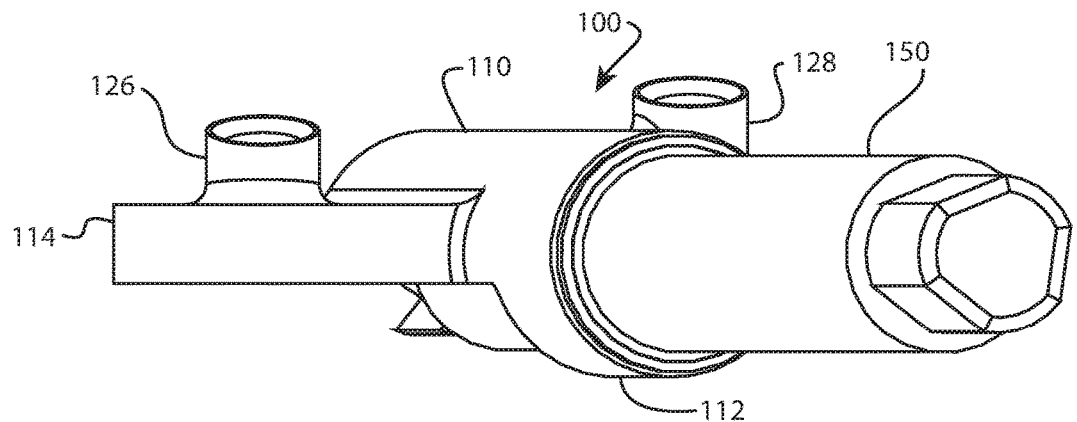
FIG. 44 is a right view of the drill guide and drill of FIG. 37.
Figure 45:
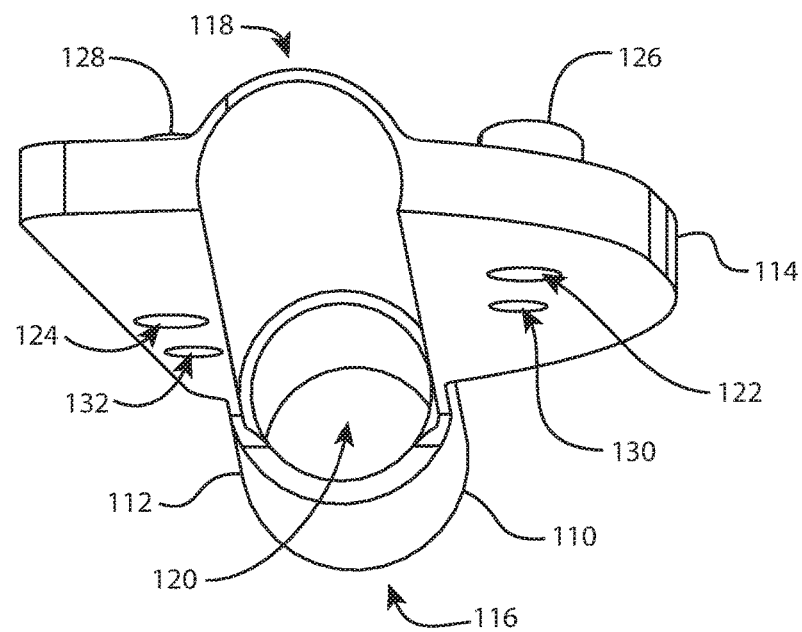
FIG. 45 is a perspective view of the drill guide of FIG. 37.

There may be a small tab 30 projecting from the rail 24. FIGS. 32 and 36 illustrate bilateral tabs. The tab may be said to protrude laterally or transversely from the rail 24. The tab deforms as the anchor is driven into the tibial tray 50, creating an interference fit. This material deformation serves to take up any relative motion between the anchor and the tibial tray as well as to lock the anchor 20 into the tray 50. The deformation may be characterized as plastic deformation, which may be at least partially irreversible. The deformation may cause galling, spot welding, and/or seizing to occur between the tab and the channel 52. Any of these adhesive phenomena may lock the anchor to the tray. There may be a physical stop 32 on the anchor to prevent over-insertion. FIGS. 28 and 29 illustrate bilateral stops. A distal tip 34 of the anchor rail may be tapered for ease of insertion into, and movement along, the channels 52. In FIGS. 26-36, physical stops 32 are located on each side of the rail 24 and extend distally from the proximal end 68. Tabs 30 are located on each side of the rail 24 near the proximal end 68, spaced apart distally from the physical stops 32. Another example may include a tab 30 on only one side of the rail. The illustrated example includes a second pair of bilateral interference tabs 31 located on each side of the rail 24 and spaced apart distally from the tabs 30. The tabs 31 are shown adjacent to a middle support 26, although they can be located anywhere along the rail 24 between the tabs 30 and the distal end 70. This arrangement may provide even greater fixation along the length of the anchor in the channel 52. Also, in other embodiments the length, height, or other dimensions of the anchor may vary.

To achieve optimal compression between the bone and the tibial tray, the anchor blade 22 may be angled divergent from the rail 24. At the leading, distal end 70 of the anchor 20, the blade 22 and the rail 24 may be farther apart than they are at the trailing, proximal end 68 of the anchor. The divergence angle 72 may be less than about 90 degrees. In some examples, the divergence angle may be less than about 15 degrees, less than about 5 degrees, or less than about 2 degrees. In the embodiment shown, the divergence angle between the blade 22 and the rail 24 is 1 degree. Divergence angles of less than 1 degree are also contemplated.

When the anchor rail 24 is inserted into the channel 52 of the tibial tray 50, the anchor blade 22 may diverge from an inferior or bone-contacting side 56 of the tray 50 at the same angle 72. Alternatively, the blade 22 may diverge from the inferior or bone-contacting side of the tray 50 at another angle, which may be greater than or less than the blade-to-rail divergence angle 72. Furthermore, the blade-to-tray divergence angle may open in the same or opposite direction as the blade-to-rail divergence angle 72.

The angle 72 between the blade 22 and the rail 24, and/or the angle between the blade and the bone-contacting side 56 may correlate to the mechanical properties of the bone into which the anchor 20 will be inserted, the desired amount of compression between the bone and the bone-contacting side, the compliance of the bone-contacting side, and/or other factors. For example, larger divergence angles may be appropriate for conditions such as: softer bone, greater compression, and/or a compliant bone-contacting side; smaller divergence angles may be appropriate for conditions such as harder or stiffer bone, less compression, and/or an unyielding bone-contacting side. The divergence angle may also correlate to the length of the anchor 20, with greater divergence angles possible with shorter anchors and smaller divergence angles suitable for longer anchors.

Figure 4:
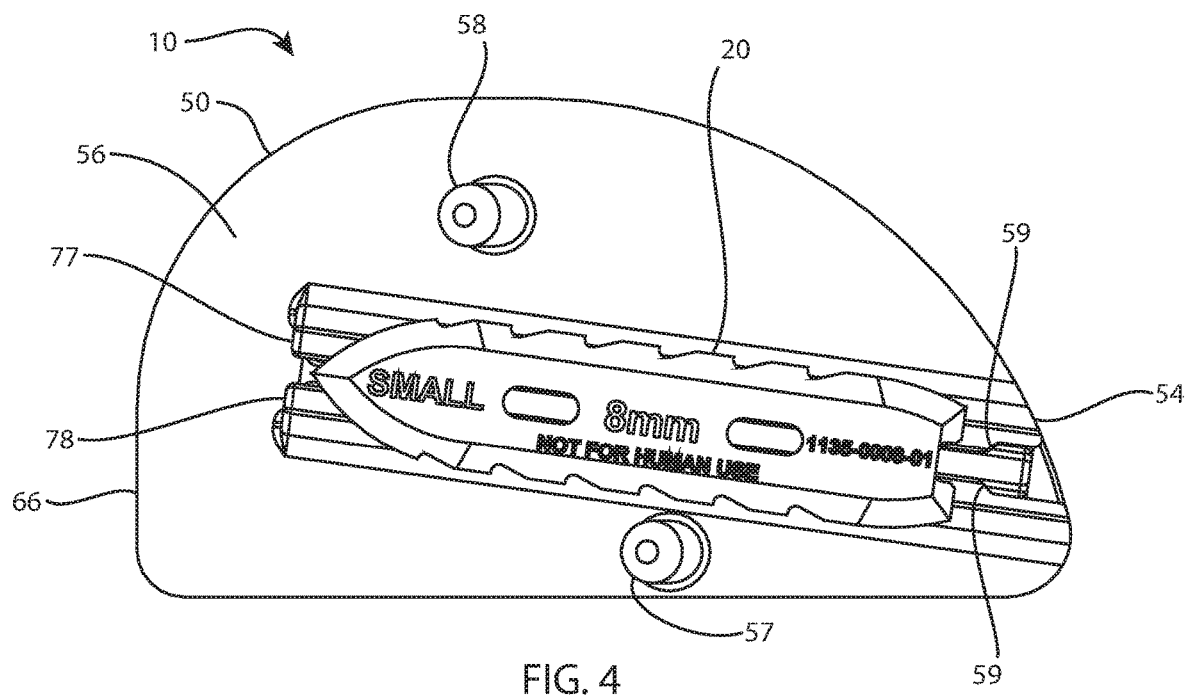
FIG. 4 is a bottom view of the tibial tray and fixation element of FIG. 1.
Figure 5:
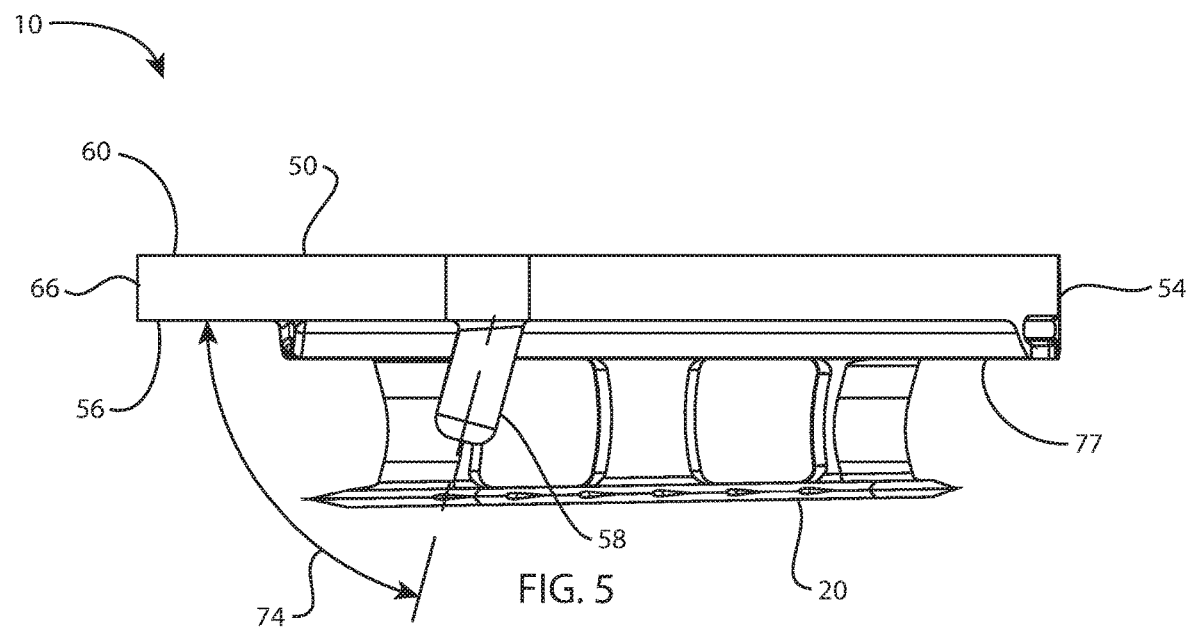
FIG. 5 is a front view of the tibial tray and fixation element of FIG. 1.
Figure 6:
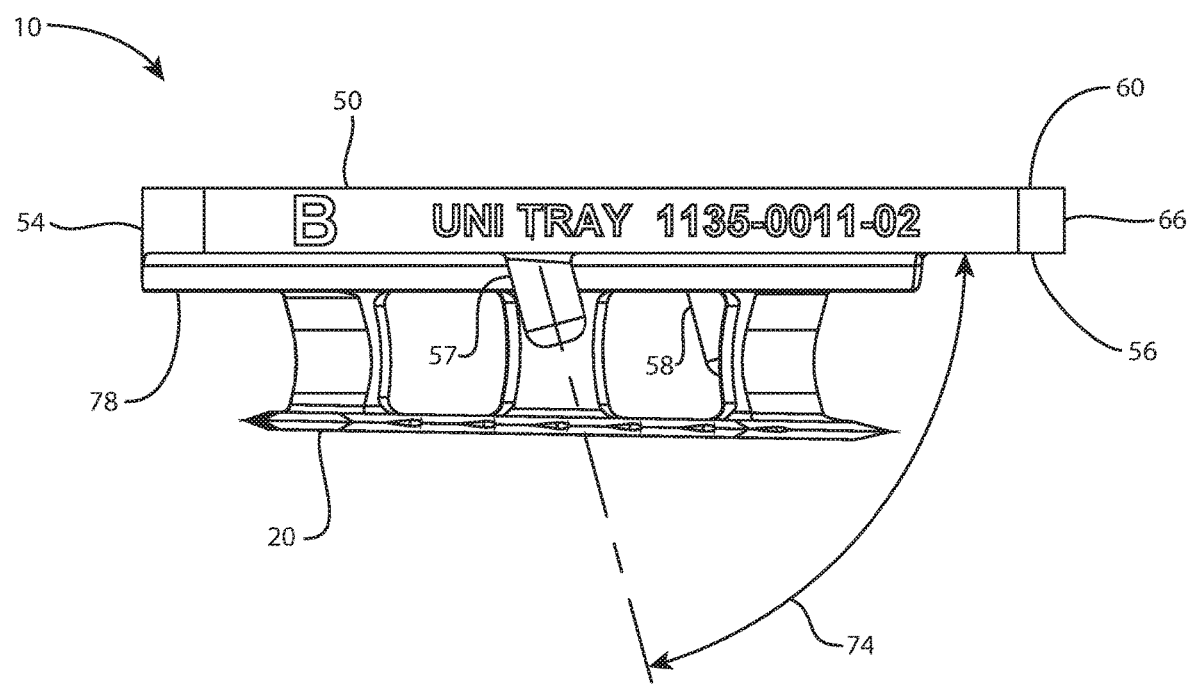
FIG. 6 is a back view of the tibial tray and fixation element of FIG. 1.
Figure 7:
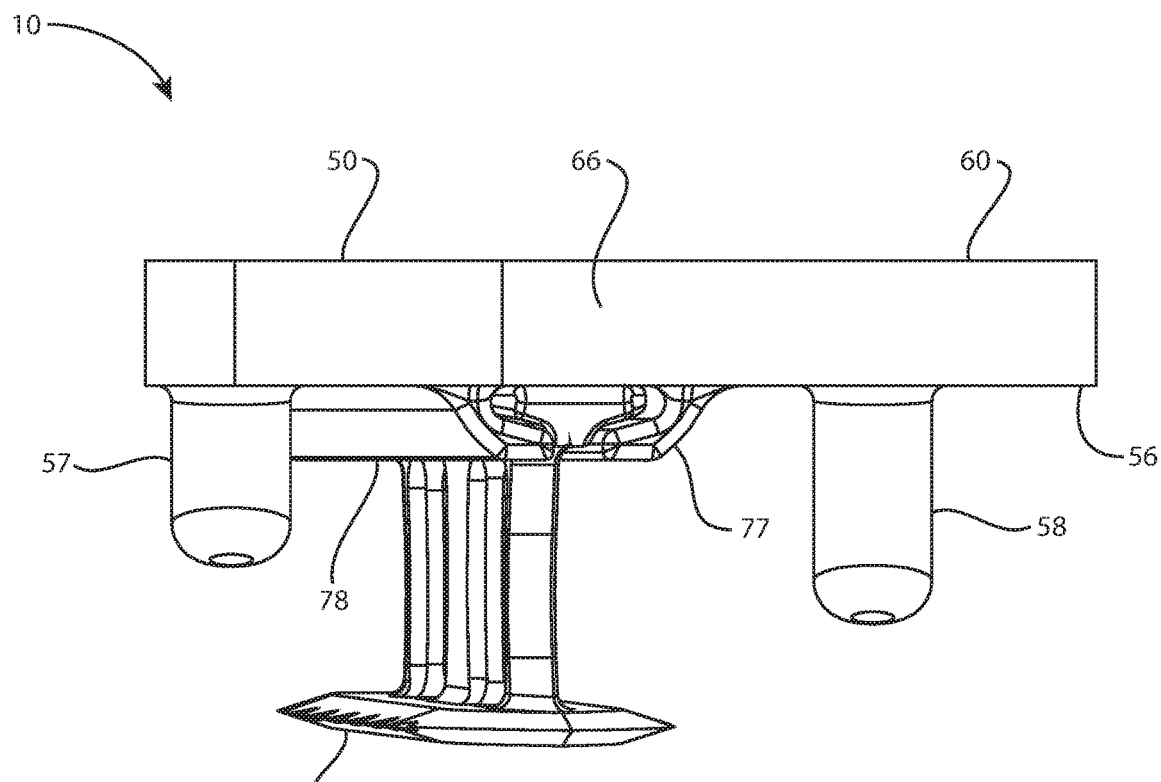
FIG. 7 is a left view of the tibial tray and fixation element of FIG. 1.
Figure 8:
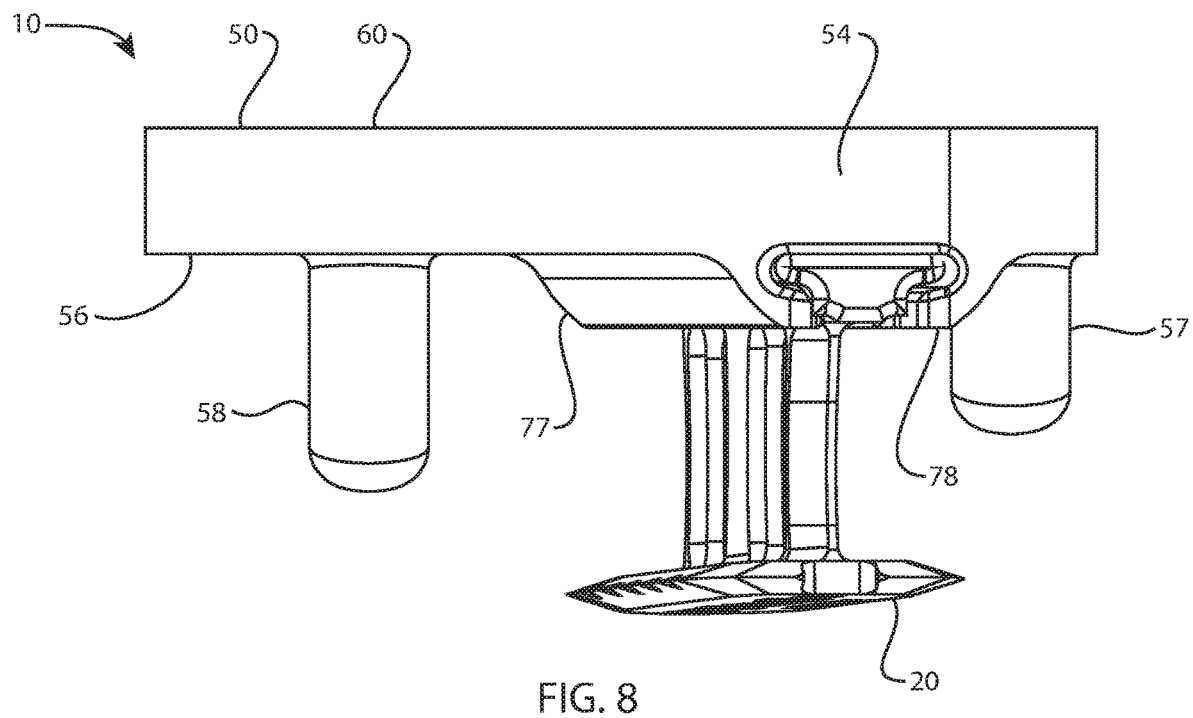
FIG. 8 is a right view of the tibial tray and fixation element of FIG. 1.
Figure 9:
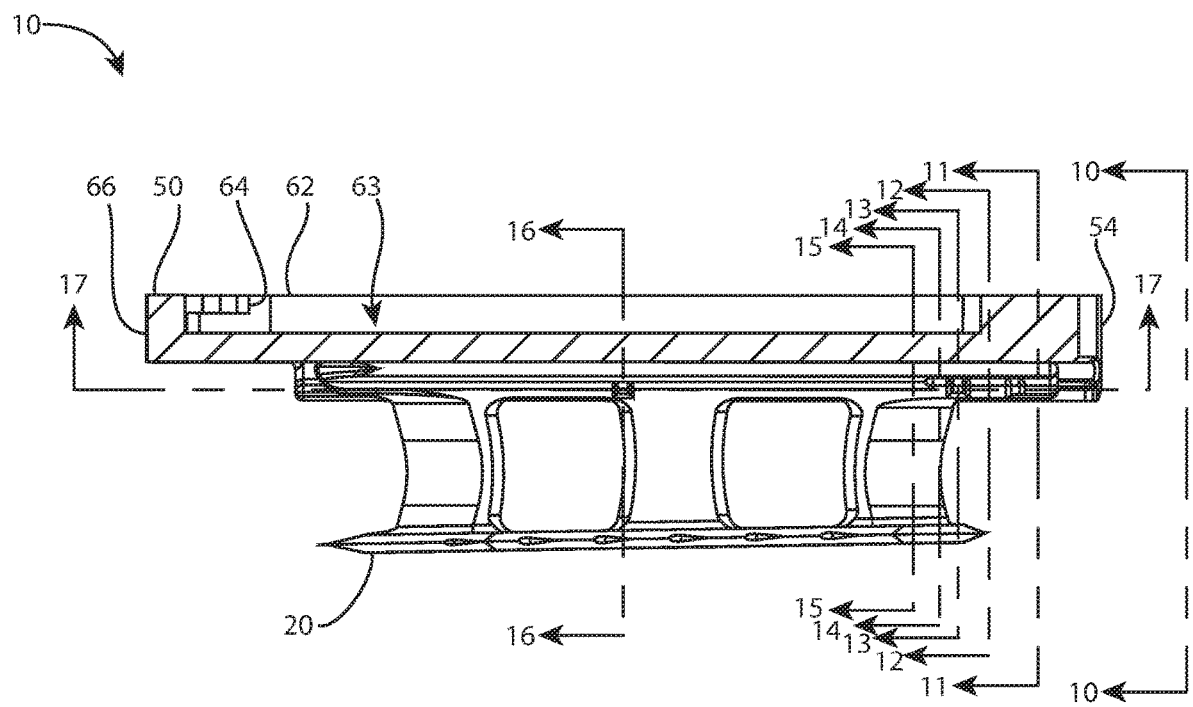
FIG. 9 is an auxiliary view of the tibial tray and fixation element of FIG. 1 perpendicular to a plane of symmetry along the length of the fixation element, the tibial tray shown in cross section taken through the plane of symmetry of the fixation element.
Figure 10:
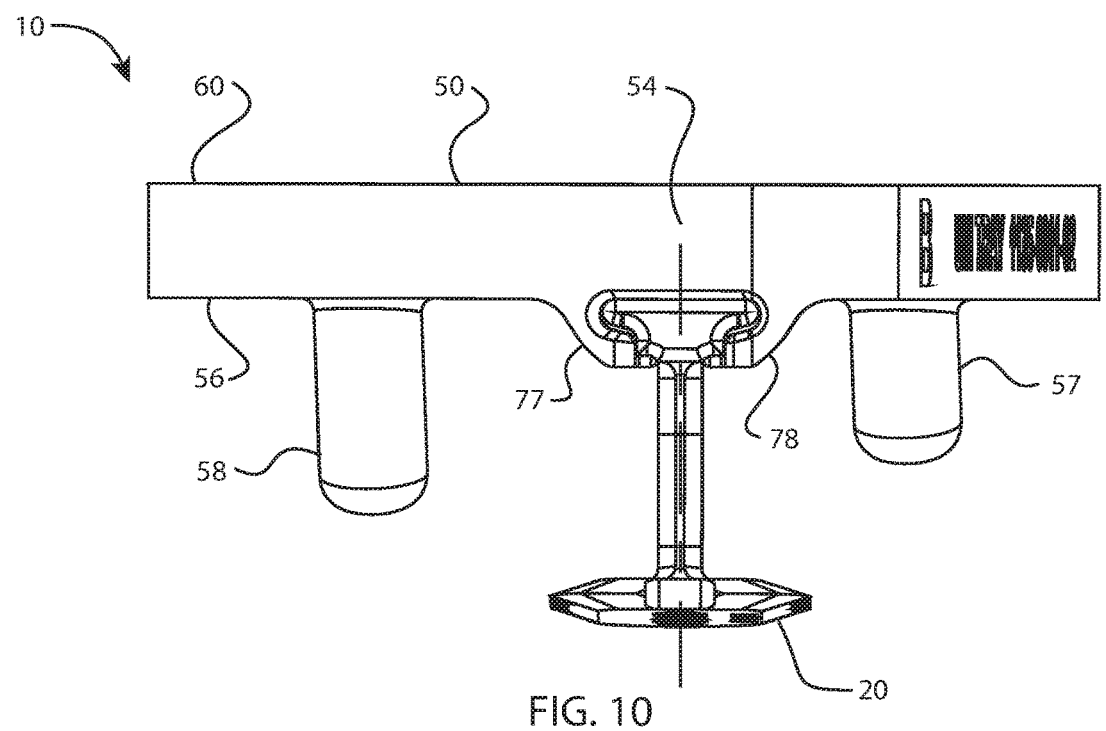
FIG. 10 is another auxiliary view of the tibial tray and fixation element of FIG. 1 taken along line 10-10 of FIG. 9 parallel to the plane of symmetry of the fixation element.
Figure 11:
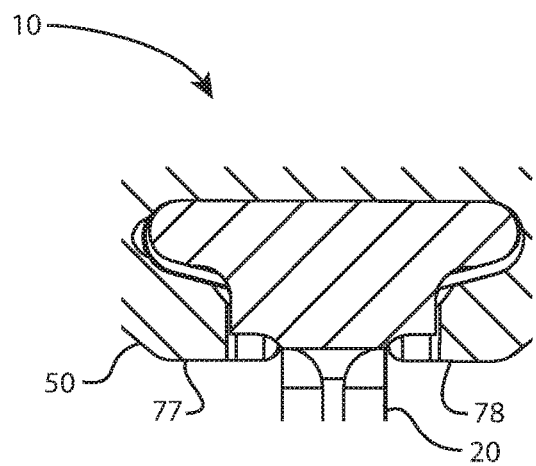
FIG. 11 is a cross sectional view of the tibial tray and fixation element of FIG. 1 taken along line 11-11 of FIG. 9.
Figure 12:
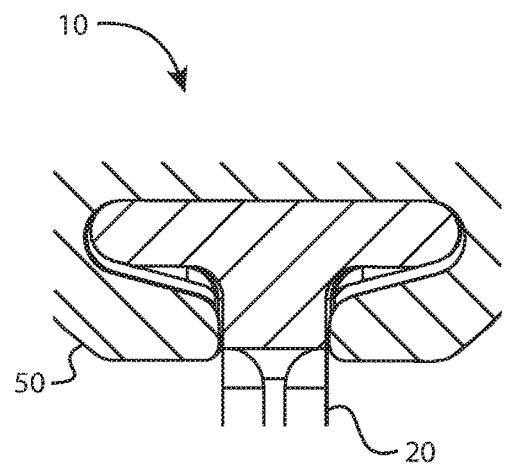
FIG. 12 is a cross sectional view of the tibial tray and fixation element of FIG. 1 taken along line 12-12 of FIG. 9.
Figure 13:
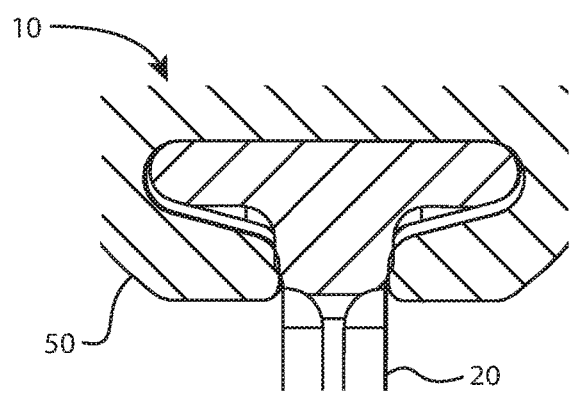
FIG. 13 is a cross sectional view of the tibial tray and fixation element of FIG. 1 taken along line 13-13 of FIG. 9.
Figure 14:
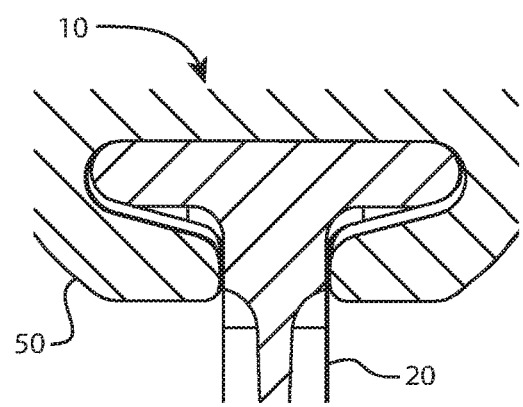
FIG. 14 is a cross sectional view of the tibial tray and fixation element of FIG. 1 taken along line 14-14 of FIG. 9.
Figure 15:
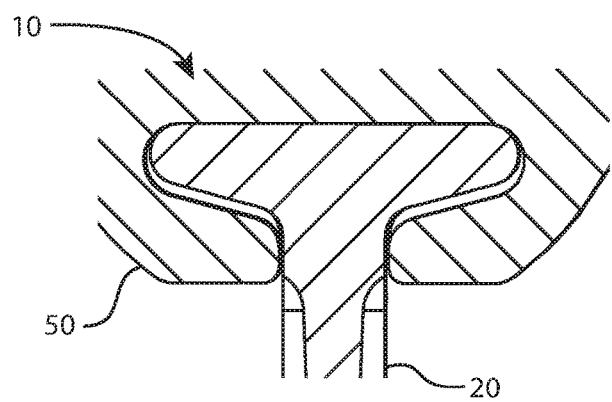
FIG. 15 is a cross sectional view of the tibial tray and fixation element of FIG. 1 taken along line 15-15 of FIG. 9.
Figure 16:
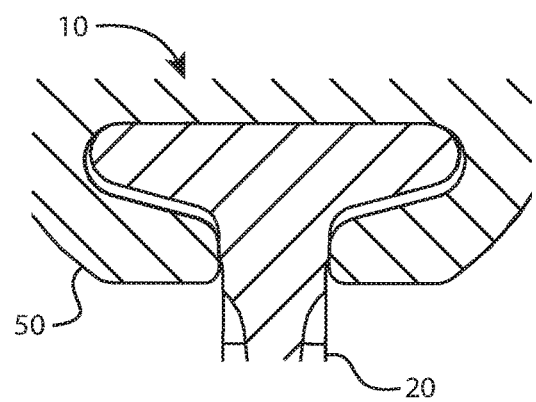
FIG. 16 is a cross sectional view of the tibial tray and fixation element of FIG. 1 taken along line 16-16 of FIG. 9.
Figure 17:
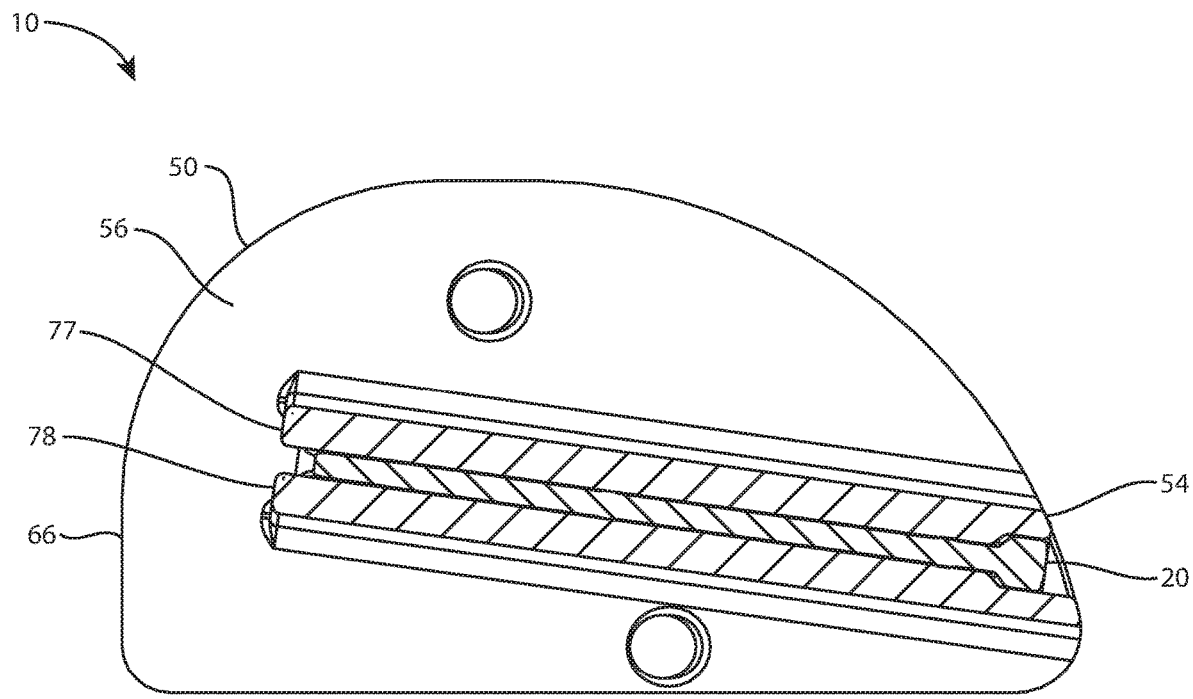
FIG. 17 is a cross sectional view of the tibial tray and fixation element of FIG. 1 taken along line 17-17 of FIG. 9.

Referring mainly to FIGS. 1-8, 10 and 19-25, the tibial tray 50 includes a bone-contacting, or inferior side 56 across which the channel 52 extends. A ridge 76 extends across the bone-contacting side 56 to provide material within which to form the channel 52. In this example, the entire channel 52 is outside the main body of the tibial tray 50, as seen best in FIGS. 22-24. In other words, the most proximal surface 53 within the channel is flush with or distal to the inferior side 56. Surface 53 may be referred to as the bottom surface of the channel. The channel 52 is thus defined between first and second walls 77, 78. At one end of each channel 52, shoulders 59 are formed in the edges of the channels 52. The shoulders 59 are illustrated as being formed in interior edges of the channel near the anterior edge 54 of the tibial tray 50. As seen in FIG. 4, when the anchor rail 24 is inserted through the channel, the shoulders 59 deform the tabs 30 and engage with the stops 32 to provide the interference fit between the anchors 20 and the tray 50, and to properly position the anchors at the correct depth relative to the tray. A peg 58 or post provides further fixation of the tray 50 in the tibia. The illustrated example includes a second peg 57 or post; any number of pegs may be present. The pegs 57, 58 protrude from the bone-contacting side 56 and form an angle 74 with the bone-contacting side. The angle 74 may be up to 90 degrees; a 75 degree angle 74 is illustrated for both pegs 57, 58. The pegs extend in an inferior-posterior direction from the bone-contacting side 56, although the pegs may extend in other directions as a matter of design choice.

The tibial tray 50 further includes a joint-facing, or superior side 60 to which an articular insert (not shown) may be mounted, or the joint-facing side 60 may include a prosthetic articular surface integrally formed with the tibial tray 50. A raised rim 62 encompasses the superior side 60, and overhangs 64 are formed on a portion of the rim 62 for engagement with an articular insert and/or instruments. The rim 62 and overhangs 64 together define a recess 63 that may receive an articular insert, and may also engage an anchor guide instrument (not shown). The articular insert or instrument may engage under the overhangs 64 to be held rigidly in the tray 50, for example by a snap fit. Tibial tray 50 may be described as a unicondylar tibial component because it is adapted to extend across a single resected tibial condyle to replace the medial or lateral condyle.

In other embodiments, the features of the tibial tray 50 may vary. For example, the peg 58 or other fixation features may vary; the size and thickness of the tray 50 may vary, the outer peripheral size and shape may vary. Different connection features for engagement with an articular insert may be incorporated. Other features of tibial trays known in the art may be included as desired. The articular insert may carry the prosthetic articular surface.

Figures 48, 49:
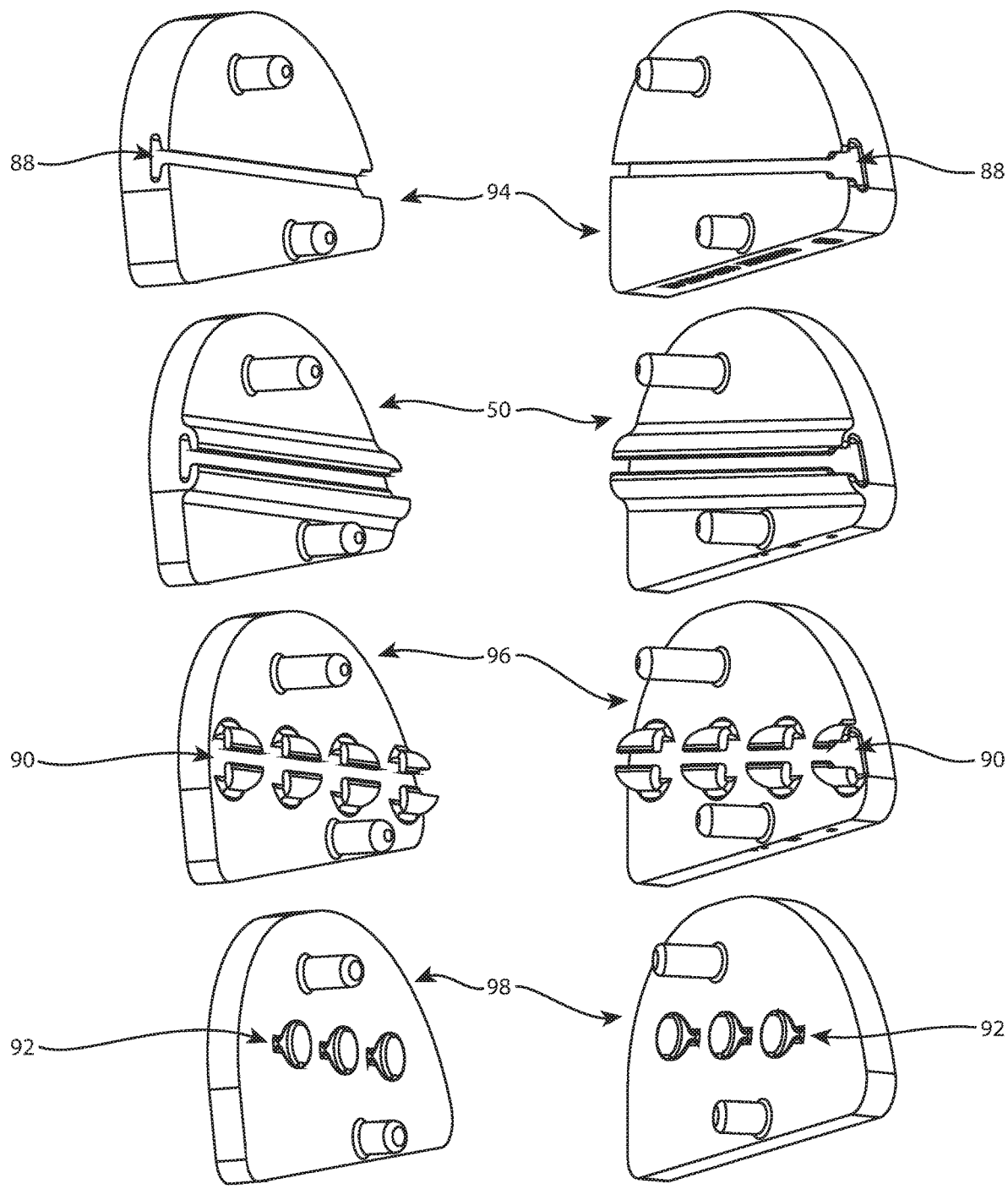
FIG. 48 is a left view of various embodiments of trays.
FIG. 49 is a right view of various embodiments of trays.

Referring to FIGS. 48-49, examples of other embodiments of the tray are shown with tibial tray 50. Tibial tray 94 includes a continuous channel 88 that is recessed entirely within the body of the tibial tray. Tibial tray 94 may share some or all of the features of the tibial tray 310 disclosed in U.S. patent application Ser. No. 13/328,592 to Bae, et al. Tibial tray 96 includes a channel 90 that includes a series of discrete channel elements within discrete ridges, or between discrete wall sections. A linear array of ridges or walls is shown. Channel 90 extends along the bone-contacting surface outside the main body of the tibial tray like channel 52. Tibial tray 98 is an example in which the negative feature of the channel is replaced by a positive connection feature 92 that includes a series of discrete connection elements, which may be referred to as posts or buttons. Not shown, the fixation element corresponding to tray 98 carries a negative feature, a channel, that is complementary to the positive connection feature 92. As in the other embodiments disclosed herein, the posts and channel may be complementary undercut shapes.

Referring to FIGS. 37-47, a guide and drill assembly 100 includes a tibial drill guide 110 and a reamer 150. The tibial drill guide 110 corresponds to the tibial tray 50. The reamer 150 is sized to correspond to the ridge 76.

Referring mainly to FIGS. 37-45, the tibial drill guide 110 includes a shaft 112 and a body 114. The shaft 112 extends between a proximal end 116 and a distal end 118 and includes a central longitudinal axis 121 and a central longitudinal hole 120 that extends entirely through the tibial drill guide 110. The body 114 corresponds to the main body of the tibial tray 50, and may be said to mimic or replicate the main body of the tibial tray 50, the perimeter of the main body, or the bone-contacting side 56. The body 114 is coupled to the distal end 118 of the shaft 112 so that the axis 121 and hole 120 are located to correspond to the height and width of the ridge 76 as viewed in FIG. 10. The body 114 includes holes 122, 124 which correspond to the pegs 58, 57, respectively, of the tibial tray 50. The holes 122, 124 may be defined by optional bosses 126, 128, respectively, to extend the length of the holes 122, 124 and/or to provide depth stops for greater accuracy in drilling holes for the pegs 58, 57. The holes 122, 124 receive a drill (not shown) sized according to the outer diameter of the pegs 58, 57. The body 114 also includes holes 130, 132 which receive bone pins (not shown) or other fasteners to secure the tibial drill guide 110 to the tibia in use.

Figure 46:
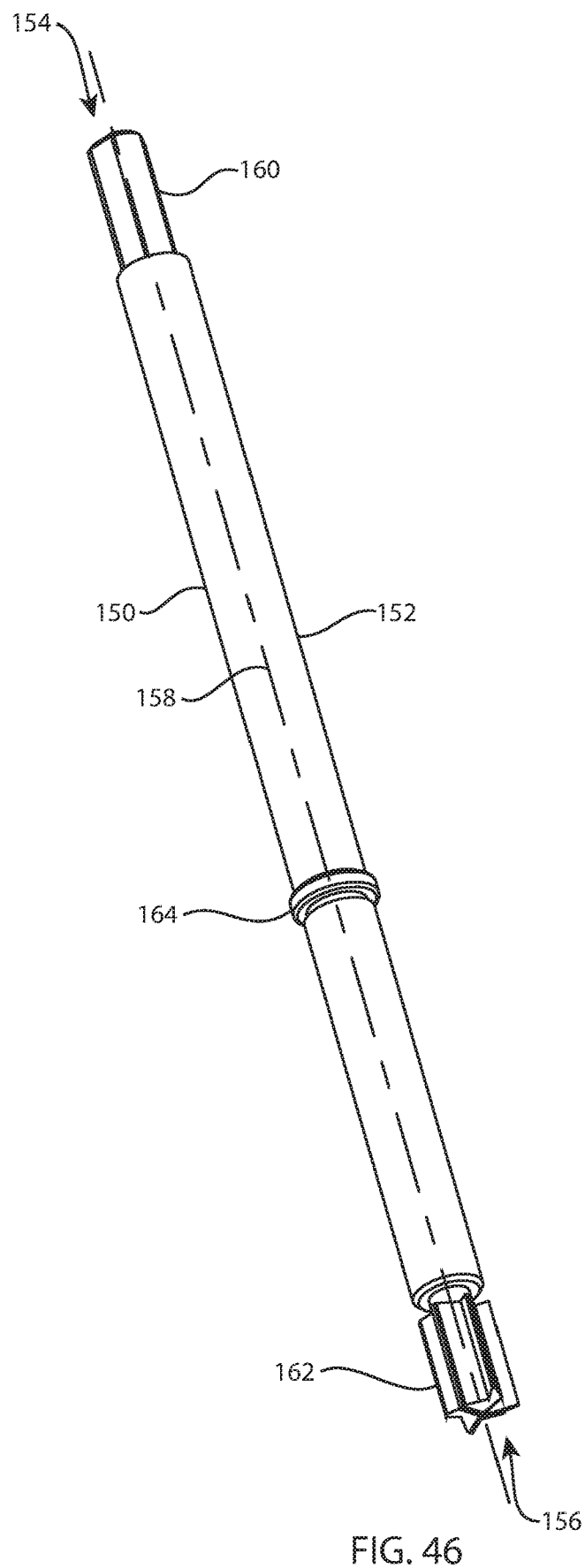
FIG. 46 is a perspective view of the drill of FIG. 37.
Figure 47:
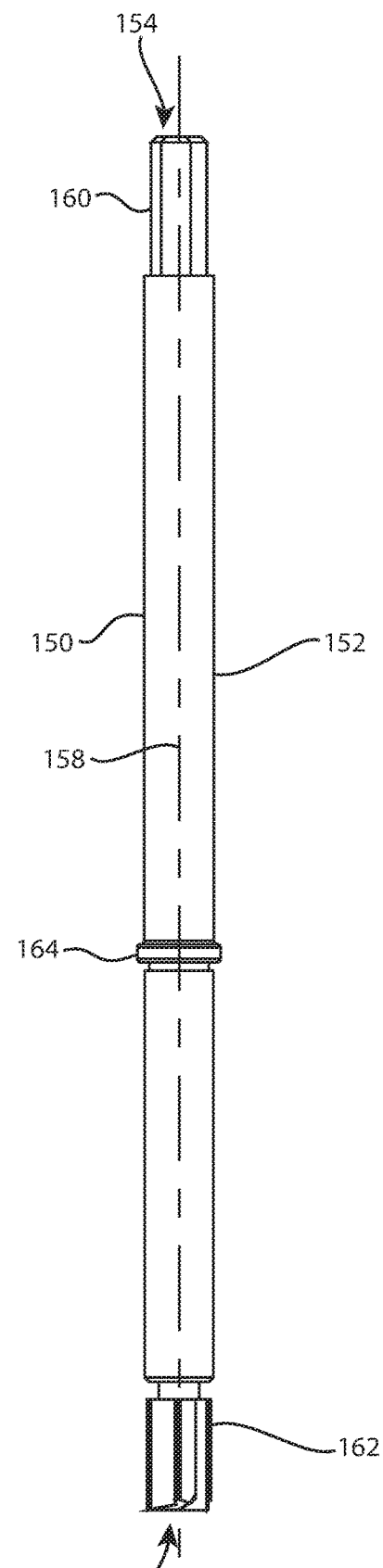
FIG. 47 is a top view of the drill of FIG. 37.

Referring mainly to FIGS. 46-47, the tibial reamer 150 includes a shaft 152 that extends between a proximal end 154 and a distal end 156 and includes a central longitudinal axis 158 about which the reamer 150 rotates in use. The proximal end 154 includes a torque drive feature 160, such as a hex key or three equilateral flats. The distal end 156 includes a cutting section 162 that may be side-cutting, end-cutting, or both. Between the torque drive feature 160 and the cutting section 162, an optional flange 164 encircles the shaft 152 to serve as a depth stop against the proximal end 116 of the shaft 112 of the tibial drill guide 110. The distance between the cutting section 162 and the flange 164 may be related to the overall length of the tibial drill guide along the axis 121 so that the cutting section 162 is prevented from extending distally across the body 114 past the end of the ridge 76. The outer diameter of the cutting section 162, as well as the outer diameter of the shaft 152 distal to the flange 164, are sized to fit in the hole 120 of the shaft 112 of the tibial drill guide 110. The outer diameter of the flange 164 is larger than the hole 120.

When the cutting section 162 is inserted into the hole 120 and advanced to be adjacent to the body 114, a portion of the cutting section 162 is exposed on the bone-contacting side of the body 114 and protrudes outwardly from the bone-contacting side of the body 114. When the bone-contacting side of the body 114 is placed against a resected bone surface, the reamer 150 is actuated (rotated about axis 158), and the reamer 150 is moved distally and proximally within the hole 120, the cutting section 162 cuts a groove across the resected bone surface that is deep enough, wide enough, and long enough to receive the ridge 76 of the tibial tray 50. The groove may receive the ridge 76 with clearance, with a line-to-line fit, or with interference (a press fit).

In a method of use, a tibia proximal end is prepared to receive the tibial tray 50. A transverse resection may be made to remove the medial or lateral proximal tibial articular cartilage. Recesses for a tray peg 58 and/or 57 may be reamed, drilled, broached, cut or otherwise prepared. The tibial tray 50 is fit onto the prepared tibia, and may be implanted with or without cement. An anchor 20 is inserted into the channel on the tray. The blade may cut into the bone as the anchor is inserted. As the anchor is inserted, the angled configuration of the anchor causes compression of the tray toward the tibia; i.e., the tray is pulled toward the tibia. The tabs, stops, and shoulders on the tray and the anchor cooperate to seat the anchor at the proper depth relative to the tray, and prevent unintentional withdrawal of the anchor. An articular insert (not shown) may be coupled to the superior surface of the tray 50, and may include an articular surface.

Figure 27:
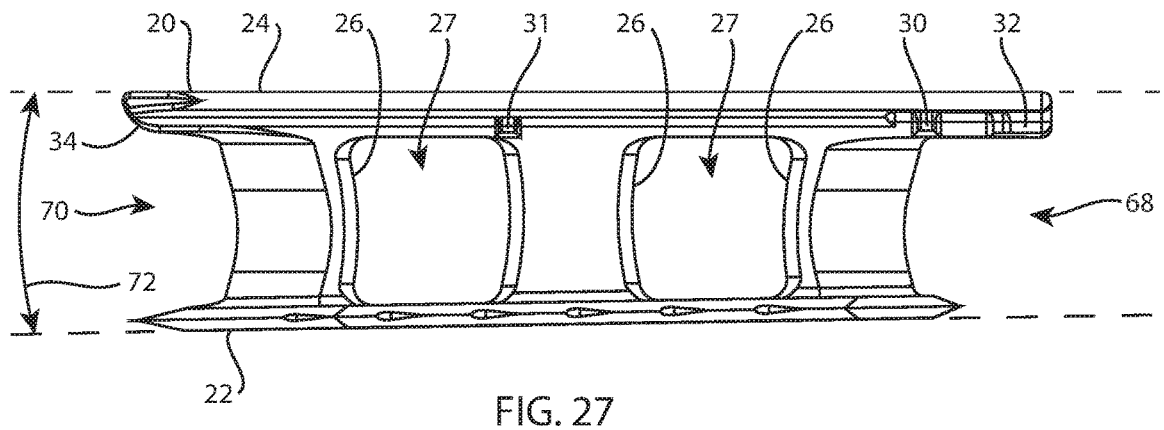
FIG. 27 is a front view of the fixation element of FIG. 1.

Referring to FIG. 27, it can be appreciated that the act of inserting anchor 20 into channel 52 and adjacent bone may be described as a sequence of events. The leading end 70 is configured so that the rail 24 and the blade 22 are the leading features, and are thus the first features to engage the channel or bone. The leading point of the blade 22 penetrates the bone. The leading support 26 is the next feature to engage, as it enters the channel and the bone. The support may be said to protrude through the bone-contacting surface, since the support extends through the open side of the channel. All leading edges of the support and blade are sharpened and obliquely oriented to reduce the effort necessary to cut through the bone.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system comprising:
   a tibial tray comprising a body having a joint-facing side and an opposite bone-facing side, wherein a ridge protrudes from and extends across the bone-facing side;
   a tibial drill guide comprising a body, wherein the tibial drill guide body corresponds to the tibial tray body, wherein a hole extends through the tibial drill guide; and
   a reamer comprising a distal cutting section, wherein the distal cutting section is received in the hole;
   wherein, when the distal cutting section is inserted into the hole and advanced to be adjacent to the tibial drill guide body, a first portion of the distal cutting section is exposed on a bone-facing side of the tibial drill guide body and protrudes outwardly from the bone-facing side of the tibial drill guide body.

2. The system of claim 1, wherein the ridge is a first ridge of a series of discrete ridges that protrude from and extend across the bone-facing side.

3. The system of claim 1, wherein an undercut channel extends across the bone-facing side within the ridge, wherein the entire undercut channel is outside the tibial tray body.

4. The system of claim 3, wherein the tibial tray joint-facing side faces proximally, wherein the tibial tray bone-facing side faces distally, wherein the entire undercut channel is flush with or distal to the tibial tray bone-facing side.

5. The system of claim 1, wherein the first portion of the distal cutting section protrudes outwardly from the bone-facing side of the tibial drill guide body to correspond to the ridge.

6. A system comprising:
   a tibial tray comprising a body having a joint-facing side and an opposite bone-facing side, wherein a first wall protrudes from and extends across the bone-facing side, wherein a second wall protrudes from and extends across the bone-facing side beside the first wall;
   a tibial drill guide comprising a body, wherein the tibial drill guide body comprises a bone-facing side that replicates the tibial tray bone-facing side, wherein a hole extends through the tibial drill guide; and
   a reamer comprising a distal cutting section, wherein the distal cutting section is received in the hole;
   wherein, when the distal cutting section is inserted into a proximal end of the hole and advanced distally next to the tibial drill guide body, a first portion of the distal cutting section is exposed on the tibial drill guide body bone-facing side and protrudes outwardly from the tibial drill guide body bone-facing side.

7. The system of claim 6, wherein the first and second walls are periodically interrupted by gaps to form a series of discrete wall sections.

8. The system of claim 6, wherein an undercut channel extends across the bone-facing side between the first and second walls, wherein the entire undercut channel is outside the tibial tray body.

9. The system of claim 8, wherein the tibial tray joint-facing side faces proximally, wherein the tibial tray bone-facing side faces distally, wherein the entire undercut channel is flush with or distal to the tibial tray bone-facing side.

10. The system of claim 6, wherein the first portion of the distal cutting section protrudes outwardly from the tibial drill guide body bone-facing side to correspond to the first and second walls.

11. A system comprising:
    an implant comprising a body having a joint-facing side and an opposite bone-facing side, wherein a first wall protrudes from and extends across the bone-facing side, wherein a second wall protrudes from and extends across the bone-facing side beside the first wall;
    a drill guide comprising a body, wherein the drill guide body comprises a bone-facing side that mimics the implant bone-facing side, wherein a hole extends through the drill guide body; and
    a reamer comprising a cutting section, wherein the cutting section is received in the hole;
    wherein, when the cutting section is inserted into the hole and advanced next to the drill guide body, a first portion of the cutting section is exposed on the drill guide body bone-facing side and protrudes outwardly from the drill guide body bone-facing side.

12. The system of claim 11, wherein the first and second walls are periodically interrupted by gaps to form a series of discrete wall sections.

13. The system of claim 11, wherein an undercut channel extends across the bone-facing side between the first and second walls, wherein the entire undercut channel is outside the implant body.

14. The system of claim 13, wherein the implant joint-facing side faces proximally, wherein the implant bone-facing side faces distally, wherein the entire undercut channel is flush with or distal to the implant bone-facing side.

15. The system of claim 11, wherein the first portion of the cutting section protrudes outwardly from the drill guide body bone-facing side to correspond to the first and second walls.

* * * * *